United States Patent [19]
Klaus et al.

[11] Patent Number: 5,986,131
[45] Date of Patent: Nov. 16, 1999

[54] RXR SELECTIVE LIGANDS

[75] Inventors: Michael Klaus, Weil am Rhein, Germany; Allen John Lovey, North Caldwell, N.J.; Peter Mohr, Basel, Switzerland; Michael Rosenberger, Caldwell, N.J.

[73] Assignee: Hoffmann-La Roche Inc., Nutley, N.J.

[21] Appl. No.: 08/953,361

[22] Filed: Oct. 17, 1997

Related U.S. Application Data

[62] Division of application No. 08/732,630, Oct. 16, 1996, abandoned, which is a division of application No. 08/468,289, Jun. 6, 1995, abandoned, which is a continuation-in-part of application No. 08/393,980, Feb. 24, 1995, abandoned.

[51] Int. Cl.$^6$ .......................... C07C 61/16; C07C 63/00; C07D 333/24; C07D 211/70
[52] U.S. Cl. .......................... 562/510; 562/405; 549/79; 546/342
[58] Field of Search .................................. 562/510, 405; 549/79; 546/342

[56] References Cited

U.S. PATENT DOCUMENTS 5,514,672  5/1996  Bazzano .................................. 514/168

FOREIGN PATENT DOCUMENTS 718 285 A2  6/1996  European Pat. Off. .

OTHER PUBLICATIONS

Paust et al, "Agent containing an all–E– or 13–Z–7,8–dehydroretinoic acid", Chem. Abs.No.93:155854, 1980.

*Primary Examiner*—Deborah C. Lambkin
*Attorney, Agent, or Firm*—George W. Johnston; William H. Epstein; Lewis J. Kreisler

[57] ABSTRACT

Novel nonatetraenoic acid derivatives which selectively bind to retinoic acid X-receptors (RXR) and which have anti-acne acitvity and which potentiate the activity of retinoids having RARα activity are disclosed.

11 Claims, 5 Drawing Sheets

RXR SELECTIVE LIGANDS

This is a division of application Ser. No. 08/732,630, filed Oct. 16, 1996, abandoned, which is a divisional of Ser. No. 08/468,289, filed Jun. 6, 1995, now abandoned, which is a continuation-in-part of application Ser. No. 08/393,980, filed Feb. 24, 1995 (now abandoned).

BACKGROUND OF THE INVENTION

Retinoic acids function through binding to a family of proteins known as the nuclear retinoic acid receptors ("RAR"). Three members of this family are designated $RAR\alpha$, $RAR\beta$, and $RAR\gamma$. 9-cis retinoic acid binds to a group of receptors known as the retinoic acid X receptors ("RXR") (Levin et al., Nature, 355:359–361 (1992); Heyman et al., Cell, 68:397–406 (1992)), while all-trans- and 13-cis-retinoic acid, which bind to $RAR\alpha$, do not. However, 9-cis retinoic acid also acts as a ligand for the RAR group of receptors, and therefore may display the undesirable side effects of all-trans and 13-cis retinoic acid. Both RAR and RXR receptors are known to form heterodimers to mediate their biological functions (Leid et al., Cell, 68:377–395 (1992); Yu et al., Cell, 67:1251–1266 (1991); Zhang et al., Nature, 355:441–446 (1992).

SUMMARY OF THE INVENTION

In accordance with this invention, it has been discovered that compounds of the formula:

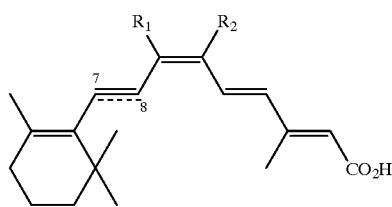

wherein the $C_7$–$C_8$ bond is a double bond or triple bond, $R_1$ and $R_2$ are independently halogen or lower alkyl when the $C_7$–$C_8$ bond is a double bond, or $R_1$ and $R_2$ are independently lower alkyl when the $C_7$–$C_8$ bond is a triple bond, or $R_1$ and $R_2$ taken together are $C_{3-13}$-alkylene in which one carbon atom may be substituted by a heteroatom selected from the group consisting of sulfur, oxygen and nitrogen, or $R_1$ and $R_2$ taken together with the carbon atoms to which they are attached are an aromatic ring having from 5–6 carbon atoms or a heteroaromatic ring having from 5–6 atoms in which one atom of $R_1$ or $R_2$ is a heteroatom selected from the group consisting of oxygen, nitrogen and sulfur and the remaining atoms of $R_1$ and $R_2$ are carbon, its pharmaceutically acceptable salts or its pharmaceutically acceptable hydrolyzable esters, potentiate the activity of retinoids having $RAR\alpha$ actitivity which are useful for the treatment of cancer, preferably leukemia and solid tumors, especially head, neck and breast tumors among solid tumors, most especially breast tumors, and are also useful, in themselves, for the treatment of dermatological conditions, especially acne and sun-damaged skin, with reduced toxicity in comparison to 9-cis- or 13-cis retinoic acid.

SHORT DESCRIPTION OF THE FIGURES

FIG. 1: Induction of differentiation of HL-60 cells with all-trans retinoic acid (RA), another $RAR\alpha$-selective retinoid (compound A, herein), and an RXR-selective retinoid (Example 4, herein $OB_{540}$ is proportional to the number of differentiated HL-60 cells).

FIG. 2: Induction of differentiation of HL-60 cells with combinations of all-trans retinoic acid (RA) and Example 4RXR Selective retinoid.

FIG. 3: Induction of differentiation of HL-60 cells with combinations of compound A and Example 4 RXR Selective retinoid.

FIG. 4A: Thymidine incorporation by B cell cultures exposed to all-trans RA or Example 4 RXR selective retinoid (Day 3). Values are relative to untreated cultures.

FIG. 4B: Thymidine incorporation by B cell cultures exposed to all-trans RA or Example 4 RXR selective retinoid (Day 4). Values are relative to untreated cultures.

FIG. 5: Inhibition of LPS-induced B cell proliferation by all-trans RA and Example 4 RXR Selective retinoid lone and in combination, at day 3 of culture.

FIG. 6: Inhibition of LPS-induced B cell proliferation by all-trans RA and Example 4 RXR selective retinoid alone and in combination, at day 4 of culture.

FIG. 7: Enhanced antiproliferative activity of a compound having $RAR\alpha$ activity (Compound B) and an RXR-selective compound (Example 6) in a breast cancer cell line.

DETAILED DESCRIPTION OF THE INVENTION

Figure 1:
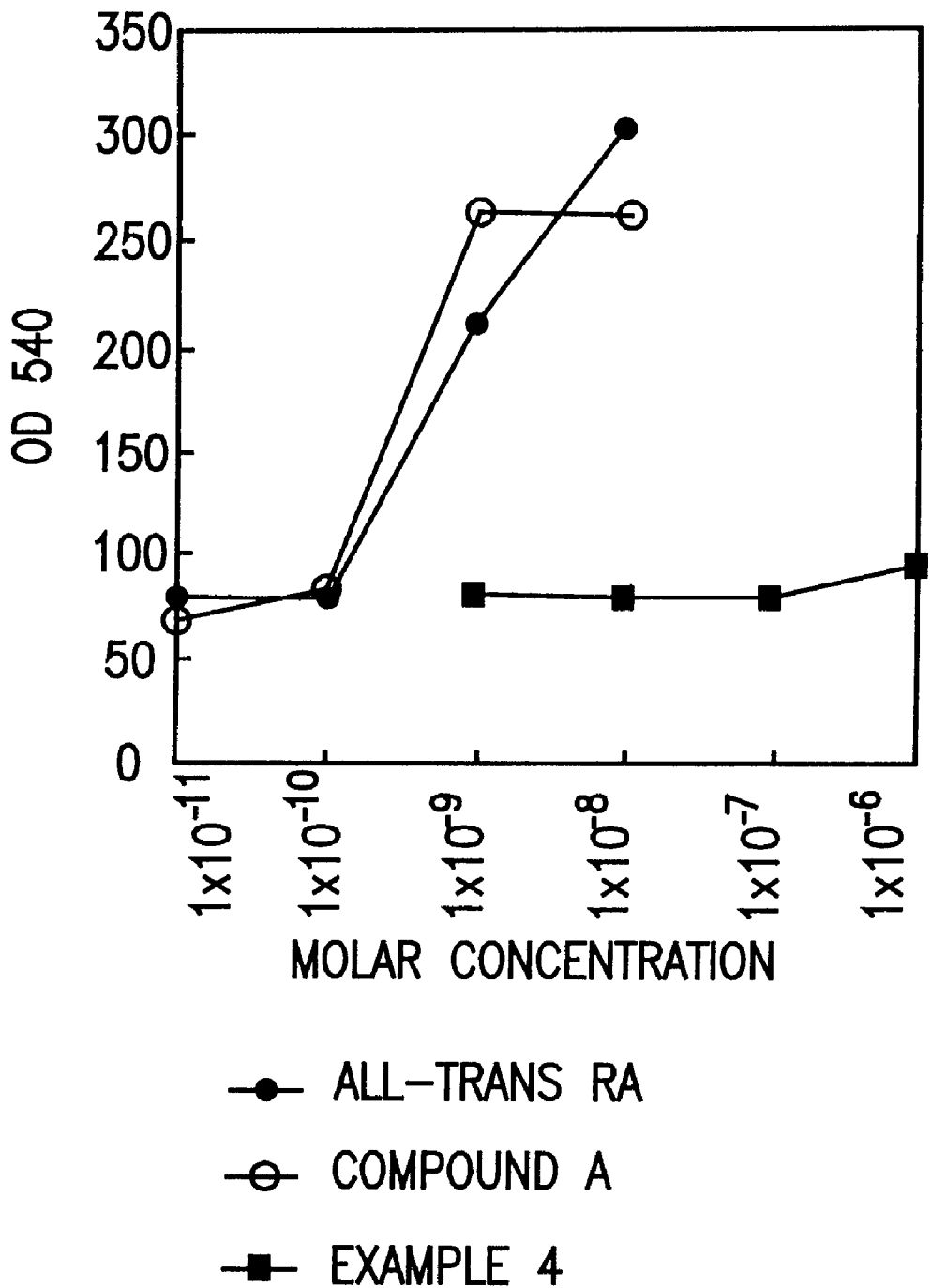

The invention comprises compounds of the formula:

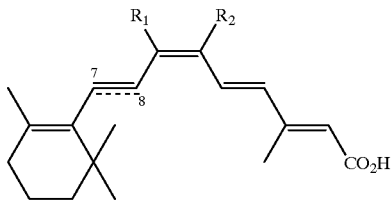

wherein the $C_7$–$C_8$ bond is a double bond or triple bond, $R_1$ and $R_2$ are independently halogen or lower alkyl when the $C_7$–$C_8$ bond is a double bond or $R_1$ and $R_2$ are independently lower alkyl when the $C_7$–$C_8$ bond is a triple bond, or $R_1$ and $R_2$ taken together are $C_{3-13}$-alkylene in which one carbon atom may be substituted. by a heteroatom selected from the group consisting of sulfur, oxygen and nitrogen, or $R_1$ and $R_2$ taken together with the carbon atoms to which they are attached are an aromatic ring having from 5–6 carbon atoms or a heteroaromatic ring having from 5–6 atoms in which one atom of $R_1$ or $R_2$ is a heteroatom selected from the group consisting of oxygen, nitrogen and sulfur and the remaining atoms of $R_1$ and $R_2$ are carbon, and the pharmaceutically acceptable salts, esters and amides. These compounds potentiate the activity of retinoids having $RAR\alpha$ activity which are useful for the treatment of cancer, especially leukemia and solid tumors, especially head, neck and breast tumors among solid tumors, most especially breast tumors, and are also useful, in themselves, for the treatment of dermatological conditions, especially acne and sun-damaged skin, with reduced toxic effects in comparison to 9-cis- or 13-cis retinoic acid.

When $R_1$ and $R_2$ taken together are $C_{3-13}$-alkylene, it is preferred that they are $C_{3-6}$-alkylene, especially $C_6$-alkylene. When $R_1$ and $R_2$ taken together with the carbon atoms to which they are attached are an aromatic ring, the preferred aromatic rings are thiophene, benzene and pyridine. $R_1$ and $R_2$ halogens may be Cl, Br, F, or I, with Br and I being preferred. $R_1$ and $R_2$ lower alkyl is $C_{1-4}$-alkyl, which may be either straight-chained or branched. The preferred lower alkyl group is methyl.

Preferred compounds of the invention are compounds of the formula:

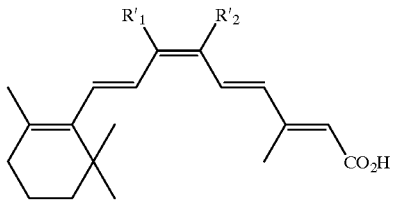

II wherein $R'_1$ and $R'_2$ are independently halogen or lower alkyl, or $R'_1$ and $R'_2$ taken together are $C_{3-13}$-alkylene in which one carbon atom may be substituted by a heteroatom selected from the group consisting of sulfur, oxygen and nitrogen, or $R'_1$ and $R'_2$ taken together with the carbon atoms to which they are attached are an aromatic ring having from 5–6 carbon atoms or a heteroaromatic ring having from 5–6 atoms in which one atom of $R'_1$ or $R'_2$ is a heteroatom selected from the group consisting of oxygen, nitrogen and sulfur and the remaining atoms of $R'_1$ and $R'_2$ are carbon, and the pharmaceutically acceptable salts, esters and amides.

When $R'_1$ and $R'_2$ taken together are $C_{3-13}$-alkylene, it is preferred that they are $C_{3-6}$-alkylene, especially $C_6$-alkylene. When $R'_1$ and $R'_2$ taken together with the carbon atoms to which they are attached are an aromatic ring, the preferred aromatic rings are thiophene, benzene and pyridine. $R'_1$ and $R'_2$ halogens may be Cl, Br, F, or I, with Br and I being preferred. $R'_1$ and $R'_2$ lower alkyl is $C_{1-4}$-alkyl, which may be either straight-chained or branched. The preferred lower alkyl group is methyl.

Other preferred compounds of the invention are compounds of the forumla:

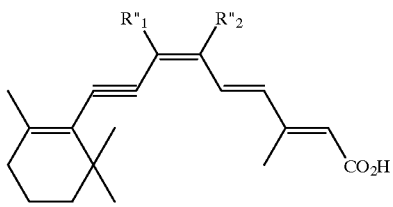

III wherein $R''_1$ and $R''_2$ are independently lower alkyl, or $R''_1$ and $R''_2$ taken together are $C_{3-13}$-alkylene in which one carbon atom may be substituted by a heteroatom selected from the group consisting of sulfur, oxygen and nitrogen, or $R''_1$ and $R''_2$ taken together with the carbon atoms to which they are attached are an aromatic ring having from 5–6 carbon atoms or a heteroaromatic ring having from 5–6 atoms in which one atom of $R''_1$ or $R''_2$ is a heteroatom selected from the group consisting of oxygen, nitrogen and sulfur and the remaining atoms of $R''_1$ and $R''_2$ are carbon, and the pharmaceutically acceptable salts, esters and amides.

When $R''_1$ and $R''_2$ taken together are $C_{3-13}$-alkylene, it is preferred that they are $C_{3-6}$-alkylene, especially $C_6$-alkylene. When $R''_1$ and $R''_2$ taken together with the carbon atoms to which they are attached are an aromatic ring, the preferred aromatic rings are thiophene, benzene and pyridine. $R''_1$ and $R''_2$ lower alkyl is $C_{1-4}$-alkyl, which may be either straight-chained or branched. The preferred lower alkyl group is methyl.

The compounds of the invention demonstrate a high degree of selectivity toward the RXR family of receptors, and are useful as antiproliferative agents and have utility for dermatological and oncological indications. In particular, the compounds of the invention inhibit the proliferation of sebocytes. Proliferation of sebocytes is known to be a cause of acne. Therefore, inhibiting of the proliferation of sebocytes is a known means of treating acne, and so the compounds of the invention are useful for the treatment of acne.

Additionally, the RXR-selective compounds of the invention, at doses at which they are inactive by themselves, increase the activity of retinoids having RARα activity, such as all-trans retinoic acid and 13-cis retinoic acid. Retinoids having RARα activity are compounds which have a biological activity which is based upon their binding to and transactivating RARα receptors. Thus, the compounds of the invention have utility as potentiators of the activity retinoids having RARα activity in treating indications where such retinoids are known to be useful. The administration of the compounds of the invention in combination with a retinoid having RARα activity allows the use of much lower doses of the retinoid, or increases the potency of the retinoid at the usual dose, for any such indications in which such a retinoid having RARα activity is known to be useful.

Thus, the invention further comprises a method of potentiating the activity of retinoids having RARα activity wherein an amount of a compound of the invention which is effective to potentiate the activity of a compound having RARα activity (preferably from 1 to 10 times the amount by weight of the compound having RARα activity) is administered to a patient in conjunction with an effective amount of the compound having RARα activity. By "in conjunction with" is meant that the RXR-selective compound of the invention may be administered as a series with the compound having RARα activity, either essentially simultaneously, preferably, but not neccessarily, combined together in a single, oral unit dosage form, or at a time prior or subsequent to the administration of the compound having RARα activity, so that the RXR-selective compound and the compound having RARα activity are simultaneously present in the blood stream of the patient so that the RXR-selective compound of the invention is present at a concentration which will potentiate the activity of the compound having RARα activity. Preferably the RXR-selective compound of the invention and the compound having RARα activity are administered no longer than four hours apart, more preferably no longer than one hour apart, and most preferably at essentially the same time.

In accordance with this invention, it has been found that the compounds of the invention potentiate the activity of retinoids having RARα activity in producing differentiation of human leukemia cells in a standard cell culture assay. Thus, the compounds of the invention have an activity which would potentiate the known activity of retinoids having RARα activity in producing regression or remission of hematological tumors, especially those tumors associated with acute promyelocytic leukemia. This treatment of leukemia would be accomplished by administering a compound of the invention systemically to a patient in conjunction with a retinoid having RARα activity which is known to be useful for retarding the progression or producing a regression of the hematological tumors. The amount will be dependent on the amount and size of the tumors and on the requirements of the patient.

Also in accordance with this invention, it has been found that the compounds of the invention potentiate the activity of retinoids having RARα activity in producing regression or remission of solid tumors, especially those tumors associated with the head and neck, and with breast cancer. Thus, the compounds of the invention have an activity which would potentiate the known activity of retinoids having RARα activity in producing regression or remission of solid tumors, especially those tumors associated with head and neck cancer, and with breast cancer. This treatment of solid tumors would be accomplished by administering a compound of the invention systemically to a patient in conjunction with a retinoid having RARα activity having activity in producing regression or remission of solid tumors, especially of the head, neck, and breast. The amount will be dependent on the amount and size of the tumors and on the requirements of the patient.

For the treatments given above, the compound of the invention is administered systemically as a composition containing the compound of the invention, optionally in combination with a compound having RARα activity, and a pharmaceutically acceptable carrier compatible with said compound(s). In preparing such composition, any conventional pharmaceutically acceptable carrier can be utilized. When the drug is administered orally, it is generally administered at regular intervals, conveniently at mealtimes or once daily.

The pharmaceutically acceptable salts include any salt chemically permissible in the art for retinoic acid and applicable to human patients in a pharmaceutically acceptable preparation. Any such conventional pharmaceutically acceptable salt of the compounds of the invention can be utilized. Among the conventional salts which can be utilized there are the base salts included, for example, alkali metal salts such as sodium or potassium, alkaline earth metal salts such as calcium or magnesium, and ammonium or alkyl ammonium salts.

In accordance with this invention the compounds of the invention can be administered in the form of its pharmaceutically acceptable hydrolyzable esters. Any pharmaceutically acceptable hydrolyzable ester can be used in the compositions and methods of this invention. Among the esters are the aromatic esters such as benzyl (OBzl) or benzyl substituted with lower alkyl, halo, nitro, thio, or substituted thio, i.e., lower alkyl, t-butyl, cyclopentyl, cyclohexyl, cycloheptyl, and 9-fluorenylmethyl.

The pharmaceutical compositions can be made up in any conventional form including: (a) a solid form for oral administration such as tablets, capsules, pills, powders, granules, and the like; and (b) preparations for topical administration such as solutions, suspensions, ointments, creams, gels, micronized powders, aerosols and the like. The pharmaceutical compositions may be sterilized and/or may contain adjuvants such as preservatives, stabilizers, wetting agents, emulsifiers, salts for varying the osmotic pressure, and/or buffers.

In accordance with this invention, the aforementioned compounds of the invention are useful in pharmaceutically acceptable oral modes. These pharmaceutical compositions of the invention contain said compound of the invention or its pharmaceutically acceptable salts and its pharmaceutically acceptable hydrolyzable esters in association with a compatible pharmaceutically acceptable carrier material. Any conventional carrier material can be utilized. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents, preferably a retinoid having RARα activity. Additional additives such as flavoring agents, preservatives, stabilizers, emulsifying agents, buffers and the like may be added in accordance with accepted practices of pharmaceutical compounding.

The pharmaceutical preparations can be made up in any conventional oral dosage form including a solid form for oral administration such as tablets, capsules, pills, powders, granules, and the like. A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician.

In orally administering to a patient the compounds of this invention for potentiating the differentiating activity of retinoids having RARα activity which are used for treating acute promyelocytic leukemia, or head, neck or breast tumors, the compound of the invention is is generally given to adults daily in an amount of about 1 to 10 times the amount of retinoid having RARα activity. The amount administered of the retinoid having RARα activity is from about 20 mg/m$^2$ to about 300 mg/m$^2$ daily, preferably from about 50 mg/m$^2$ to about 100 mg/m$^2$ daily, with the precise dosage being varied depending upon the size and weight of the patient. In general, the combination treatment is carried out for a period of about three months.

The compounds of the invention or their pharmaceutically acceptable salts or hydrolyzable esters and the retinoids having RARα activity may be administered separately in accordance with the invention, but are preferably administered as an oral composition containing the compound of the invention, its pharmaceutically acceptable salts or esters, in combination with the retinoid having RARα activity in an amount sufficient for the combination to treat acute promyelocytic leukemia or head, neck or breast tumors.

Generally the preferred unit oral dosage form is tablets or capsules containing from 10 to 50 mg of the retinoid having RARα activity and a compound of the invention in an amount from 1 to 10 times the amount of the retinoid having RARα activity, its pharmaceutically acceptable salts or its pharmaceutically acceptable hydrolyzable esters. Thus, the amount of the compound of the invention in each tablet or capsule can be from 10 to 500 mg. These tablets or capsules can be administered once or twice daily depending upon the weight and size of the patient.

In accordance with this invention, the topical and oral administration of the compounds of the invention, their pharmaceutically acceptable salts and their pharmaceutically acceptable hydrolyzable esters, are effective in treating all forms of acne such as inflammatory and non- inflammatory.

For topical administration to the skin, compositions containing a compound of the invention in a pharmaceutically acceptable carrier are preferably prepared as ointments, tinctures, creams, gels, solutions, lotions, sprays, suspensions, shampoos, hair soaps, and the like. In fact, any conventional composition utilized for application to the scalp or skin can be utilized in accordance with this invention. Among the preferred methods of applying the composition containing the active ingredient of the invention is to apply the active ingredient of the invention in the form of a gel, lotion or cream. The pharmaceutical preparation for topical administration to the skin can be prepared by mixing the aforementioned active ingredient of the invention with non-toxic, therapeutically inert, solid or liquid carriers customarily used in such preparations. These preparations should contain at least about 0.05 percent by weight of the active ingredient of the invention based upon the total weight of the composition. Since the active ingredient of the invention is relatively non-toxic and non-irritating, it may be used in topical compositions in amounts exceeding 3.0% percent. It is preferred that these preparations contain about 1 to 2% percent by weight of the active ingredient of the invention based upon the total weight of the composition. It is also preferred to apply these preparations once or twice daily to the skin. These preparations can be applied according to the need of the patient. In carrying out this invention, the active ingredient of the invention can also be applied in an aqueous solution or an alcohol solution such as ethyl alcohol.

In preparing the topical preparations described above additives such as preservatives, thickeners, perfumes and the like conventional in the art of pharmaceutical compounding of topical preparations can be used. In addition, conventional antioxidants can be incorporated into the topical preparations containing the aforementioned active agent of the invention. Among the conventional antioxidants which can be utilized in these preparations are included N-methyl-α-tocopherolamine, tocopherols, butylated hydroxyanisole, butylated hydroxytoluene, ethoxyquin and the like.

Conventional perfumes and lotions generally utilized in topical preparations for the hair can be utilized in accordance with this invention. Furthermore, if desired, conventional emulsifying agents can be utilized in the topical preparations of this invention.

Ointment formulations containing the active ingredient of the invention may comprise admixtures of a semi-solid petroleum hydrocarbon with a solvent dispersion of the active ingredient of the invention.

Cream compositions containing the active ingredient of the invention preferably comprise emulsions formed from a water phase of a humectant, a viscosity stabilizer and water, an oil phase of a fatty acid alcohol, a semi-solid petroleum hydrocarbon and an emulsifying agent and a phase containing the active ingredient of the invention dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are preferably derived from the reduction of a long-chain saturated fatty acid of at least about 14 carbon atoms. Cream-base pharmaceutical formulations containing the active ingredient of the invention may be composed of, for example, aqueous emulsions containing a fatty acid alcohol, semi-solid petroleum hydrocarbon, 1,2-ethyleneglycol and an emulsifying agent.

Generally, treatment of acne, whether inflammatory or noninflammatory, may be affected by orally administering to a patient from 0.1–10 mg/kg of a compound of the invention once or twice daily. Treatment of acne may be affected by topically applying a topical composition containing a compound of the invention in a amount from about 0.05% to about 3% by weight, preferably about 1% to about 2% by weight, once or twice daily.

The dosage for treatment typically depends on the route of administration, the age, weight, size and disease condition of the individual.

Preferred compounds of the invention are:
(2E,4E,6Z,8E)-3,6,7-trimethyl-9-(2,6,6-trimethyl-1-cyclohexen-1-yl)-2,4,6,8-nonatetraenoic acid;
(2E,4E.)-3-methyl-5-(2-(2-((E)-2-(2,6,6-trimethyl-1-cyclohexen-1-yl)ethenyl)-1-cyclohexen-1-yl)-2,4-pentadienoic acid;
(all-E)-6-bromo-3,7-dimethyl-9-(2,6,6-trimethyl-1-cyclohexen-1-yl)-2,4,6,8-nonatetraenoic acid;
(All-E)-6-iodo-3,7-dimethyl-9-(2,6,6-trimethyl-1-cyclohexen-1-yl)-2,4,6,8-nonatetraenoic acid;
(All-E-)-6-chloro-3,7-dimethyl-9-(2,6,6-trimethyl-1-cyclohexen-1-yl)-2,4,6,8-nonatetraenoic acid
(2E,4E)-3-methyl-5-(2-((E)-2(2,6,6-trimethyl-1-cyclohexen-1-yl)ethenyl)-1-cyclopenten-1-yl)-2,4-pentadienoic acid;
(2E,4E)-3-methyl-5-(2-((E)-2(2,6,6-trimethyl-1-cyclohexen-1-yl)ethenyl)-1-cyclohepten-1-yl)-2,4-pentadienoic acid;
(2E,4E)-3-methyl-5-(2-((E)-2(2,6,6-trimethyl-1-cyclohexen-1-yl)ethenyl)-1-cycloocten-1-yl)-2,4-pentadienoic acid;
(2E,4E)-3-methyl-5-(2-(2-((E)-2-(2,6,6-trimethyl-1-cyclohehen-1-yl)ethenyl)-1-phenyl)-2,4-pentadienoic acid;
(2E,4E)-3-methyl-5-(3-((E)-2-(2,6,6-trimethyl-1-cyclohexen-1-yl)ethenyl)-2-thienyl)-2,4-pentadienoic acid;
(2E,4E)-3-methyl-5-(2-((E)-2-(2,6,6-trimethyl-1-cyclohexen-1-yl)ethenyl)-3-thienyl)-2,4-pentadienoic acid;
(2E,4E)-3-methyl-5-(4-((E)-2-(2,6,6-trimethyl-1-cyclohexen-1-yl)ethenyl)-3-thienyl)-2,4-pentadienoic acid;
(2E,4E)-3-methyl-5-[2-(2,6,6-trimethyl-cyclohex-1-enylethynyl)-cyclopent-1-enyl]-penta-2,4-dienoic acid;
(2E,4E)-3-Methyl-5-[2-(2,6,6-trimethyl-cyclohex-1-enylethynyl)-cyclohept-1-enyl]-penta-2,4-dienoic acid; and
(2E,4E)-3-Methyl-5-[2-(2,6,6-trimethyl-cyclohex-1-enylethynyl)-phenyl]-penta-2,4-dienoic acid.

Methods for determining the binding and transactivation properties of retinoids with regard to the RAR receptors and RXR receptors are known in the art, e.g., Levin et al., *Nature*, 355:359–361 (Jan. 23, 1992); Allenby et al., *Proc. Natl. Acad. Sci. USA*, 90:30–34 (January, 1993); Allenby et al., *J. Biol. Chem.*, 269:16689–16695 (Jun. 17, 1994). Methods essentially as described in those publications were used to determine the binding and transactivation properties of retinoids reported in the Examples herein.

The activity of the compounds of the invention for use in treating acne may be determined by any conventional means. For example, the ability of the compounds of the invention to inhibit the proliferation of sebocytes is a standard model of acne treatment. The sebocyte antiproliferative activity of the compounds of the invention maybe determined in accordance with the procedure of Example 20(1).

Additionally, the ability of the compounds of the invention to reduce the size of Rhino mouse utricles is another standard model of acne treatment. This activity may be determined in accordance with the procedure of Example 20(2).

Further, the ability of the compounds of the invention to reduce the size of Syrian Golden Hamster sebaceous glands is another standard model of acne treatment. This activity may be determined in accordance with the procedure of Example 20(3).

The ability of the compounds of the invention to potentiate the RARα activity of retinoids may be determined by any conventional means. Thus, the ability of the compounds of the invention to potentiate the RARα activity of retinoids may be determined by measuring the activity of the combination of a compound of the invention with a retinoid having RARαactivity in a standard screening assay which has known relevance to a disease state for which the retinoid is known to be useful for treatment. The reduction of the concentration of the retinoid having RARα activity needed to obtain a particular level of activity, or an increase in activity of the retinoid at a constant concentration, would demonstrate the potentiating activity of the compounds of the invention where the concentration of the compound of the invention is one at which the compound of the invention has little or no activity by itself.

For example, the results shown below of the ability of the compounds of the invention to potentiate the activity of retinoids in differentiating HL-60 cells (a standard model of human leukemia) demonstrate the potentiating activity of the compounds of the invention. The ability of the compounds of the invention to potentiate the activity of retinoids having RARα activity in differentiating HL-60 cells may be carried out in accordance with Example 18.

Additionally, the results shown below of the ability of the compounds of the invention to potentiate the activity of retinoids having RARα activity in inhibiting mouse B cell activation (a standard model of immunosuppresion) demonstrates the potentiating activity of the compounds of the invention. The ability of the compounds of the invention to potentiate the activity of retinoids in inhibiting mouse B cell activation may be carried out in accordance with Example 19.

Further, the results shown below of the ability of the compounds of the invention to potentiate the activity of retinoids having RARα activity in inhibiting the growth of a breast carcinoma cell line (a model of a solid tumor) demonstrates the potentiating activity of the compounds of the invention. The ability of the compounds of the invention to potentiate the activity of retinoids in inhibiting the growth of a breast carcinoma cell line may be carried out in accordance with Example 21.

The compounds of the invention may be prepared by any conventional means. The preferred methods are illustrated in the following schemes:

SCHEME 1a

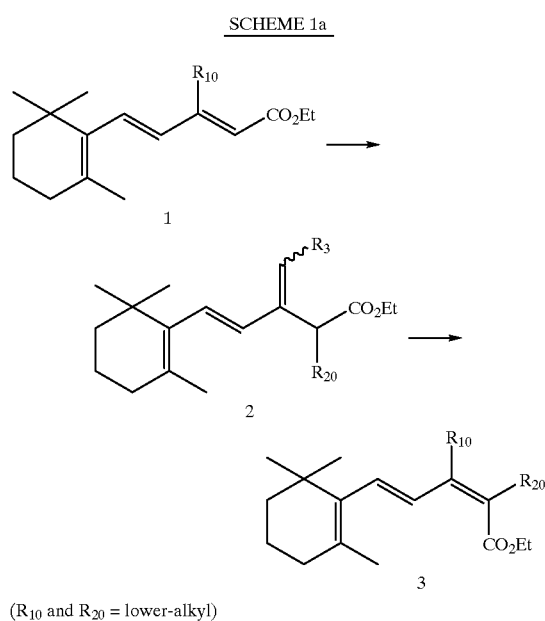

($R_{10}$ and $R_{20}$ = lower-alkyl)

SCHEME 1b

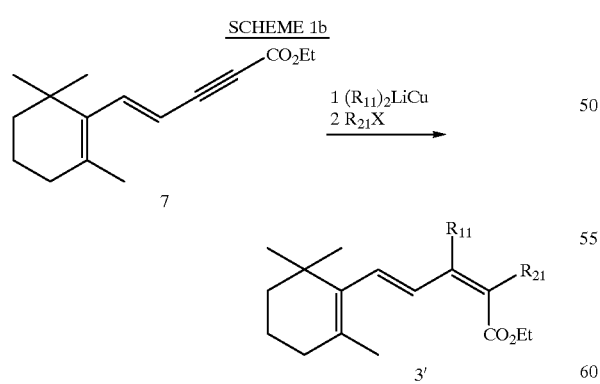

($R_{11}$ = lower-alkyl; $R_{21}$ = halogen)

SCHEME 1c

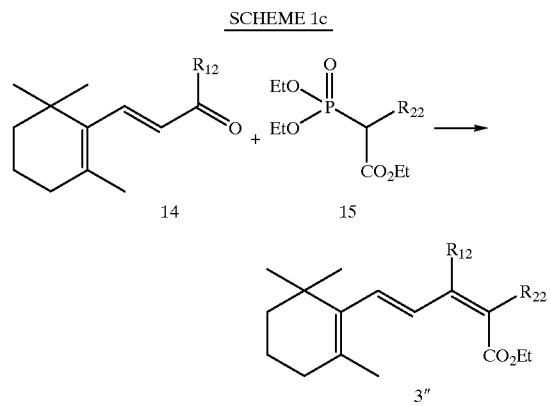

($R_{12}$ = lower-alkyl or halogen; $R_{22}$ = lower-alkyl, F or Cl)

SCHEME 1d

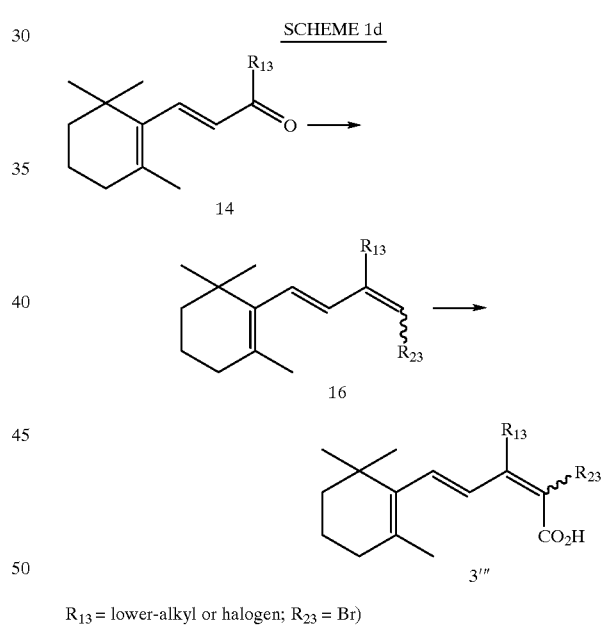

$R_{13}$ = lower-alkyl or halogen; $R_{23}$ = Br)

SCHEME 2
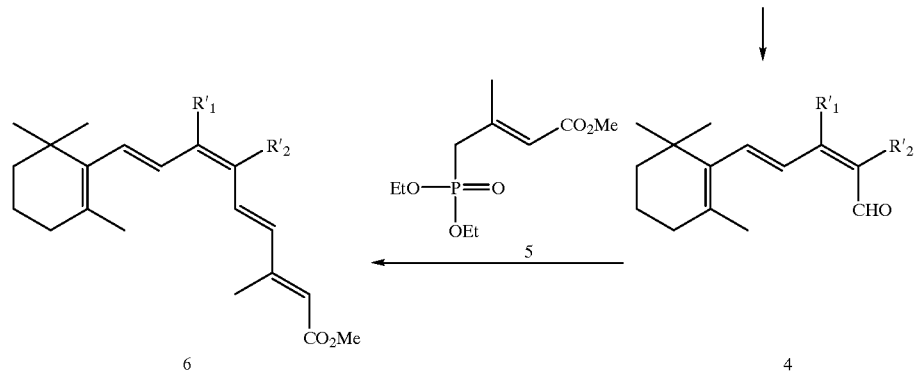
SCHEME 3
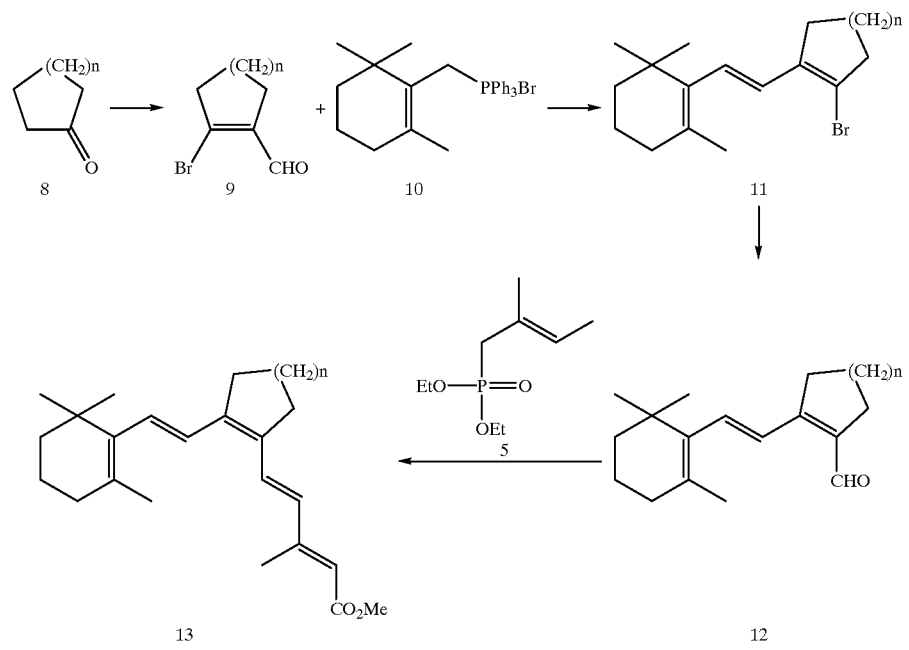

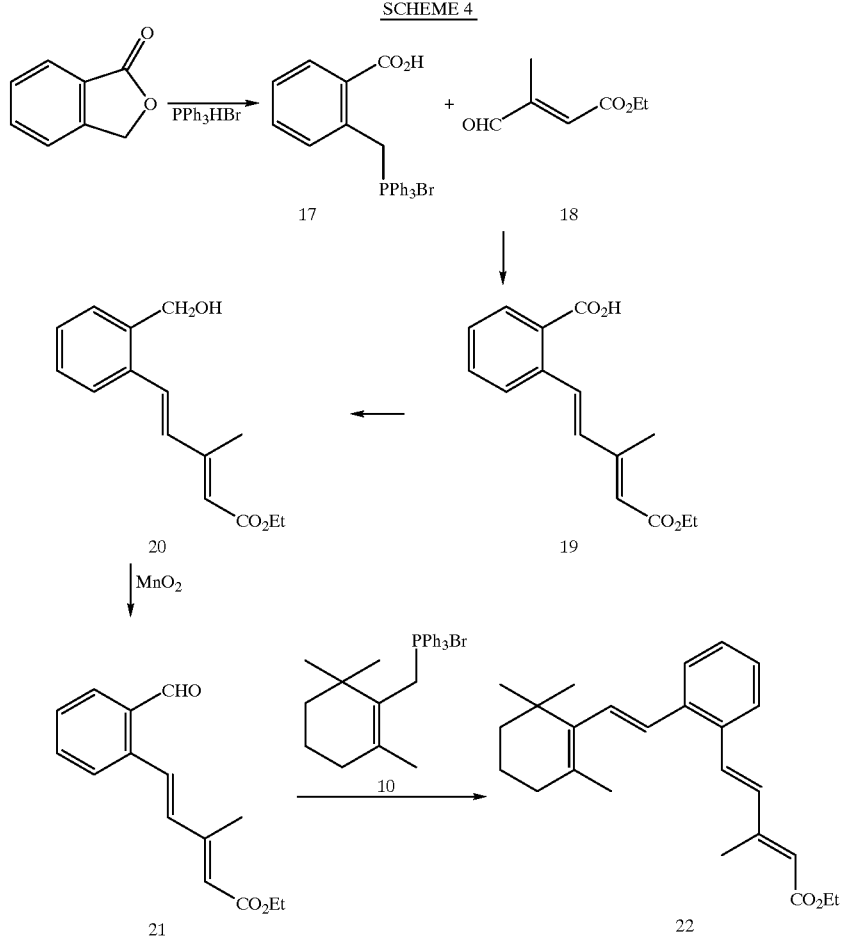
SCHEME 4
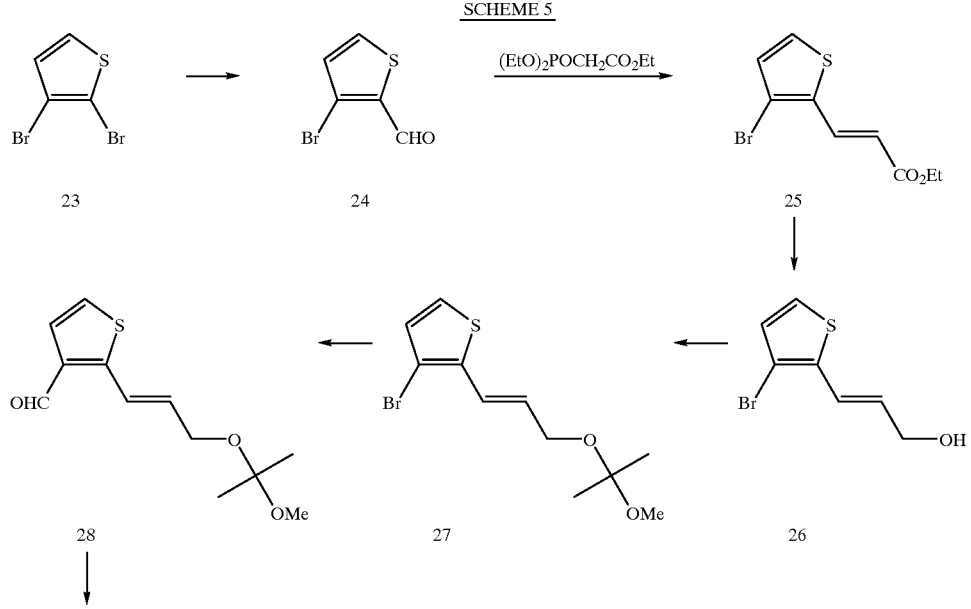
SCHEME 5

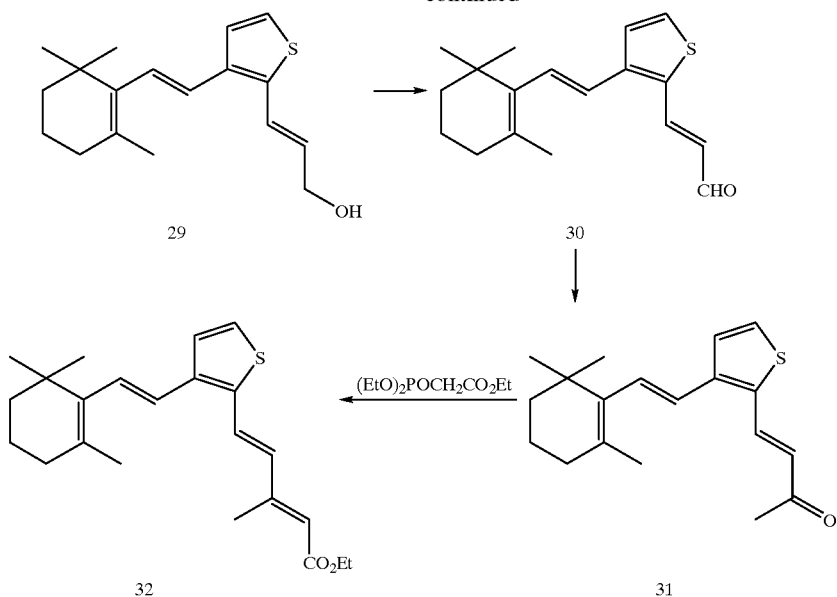
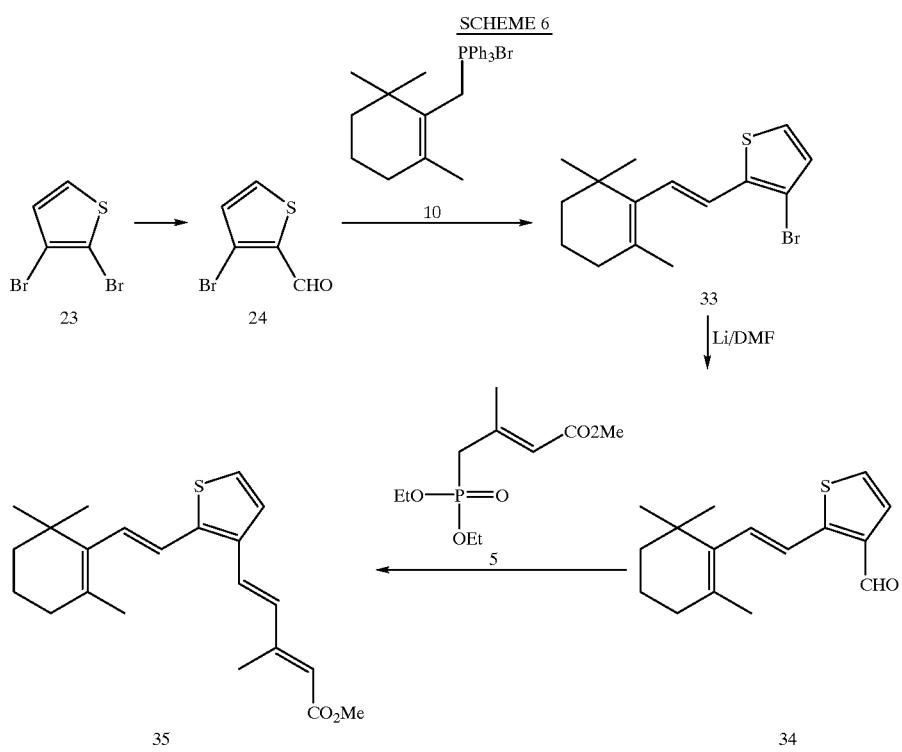

SCHEME 7
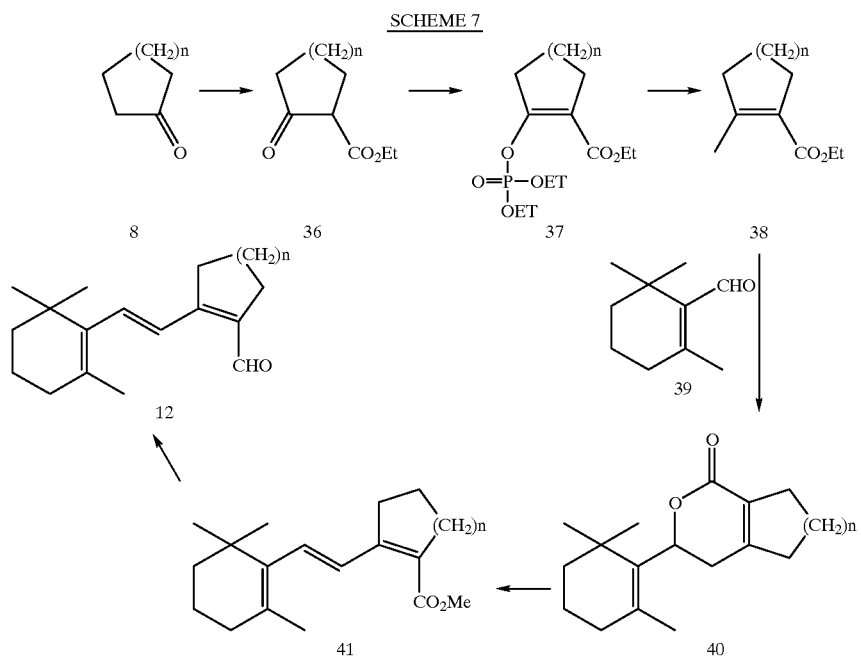
SCHEME 8
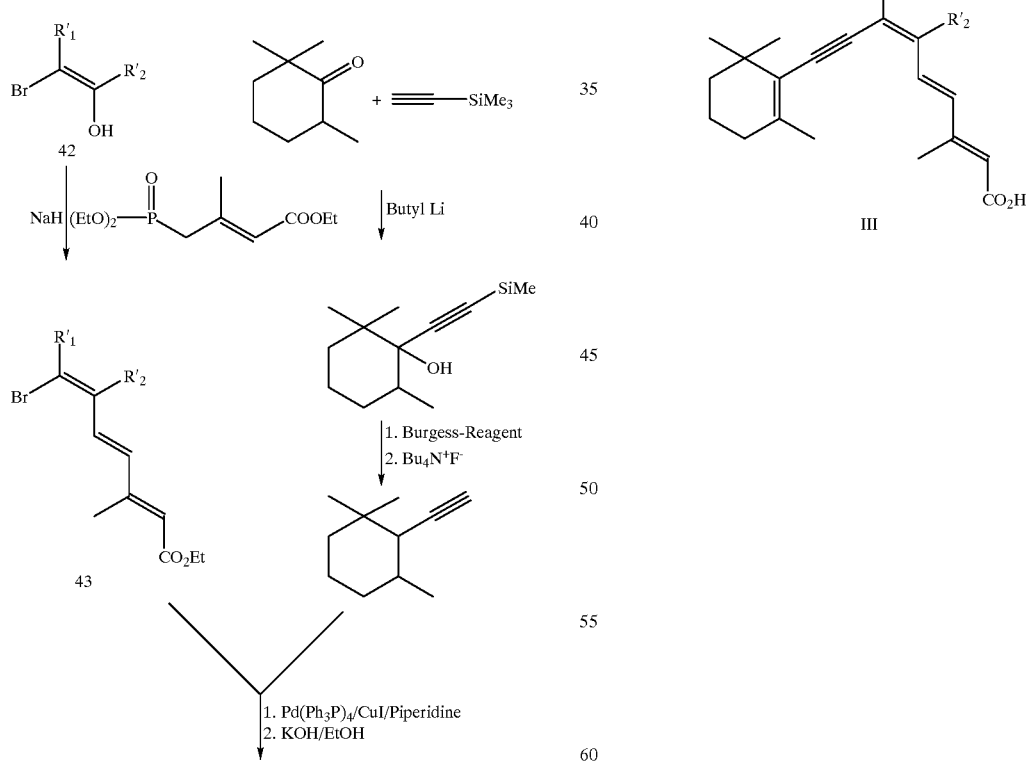

SCHEME 9

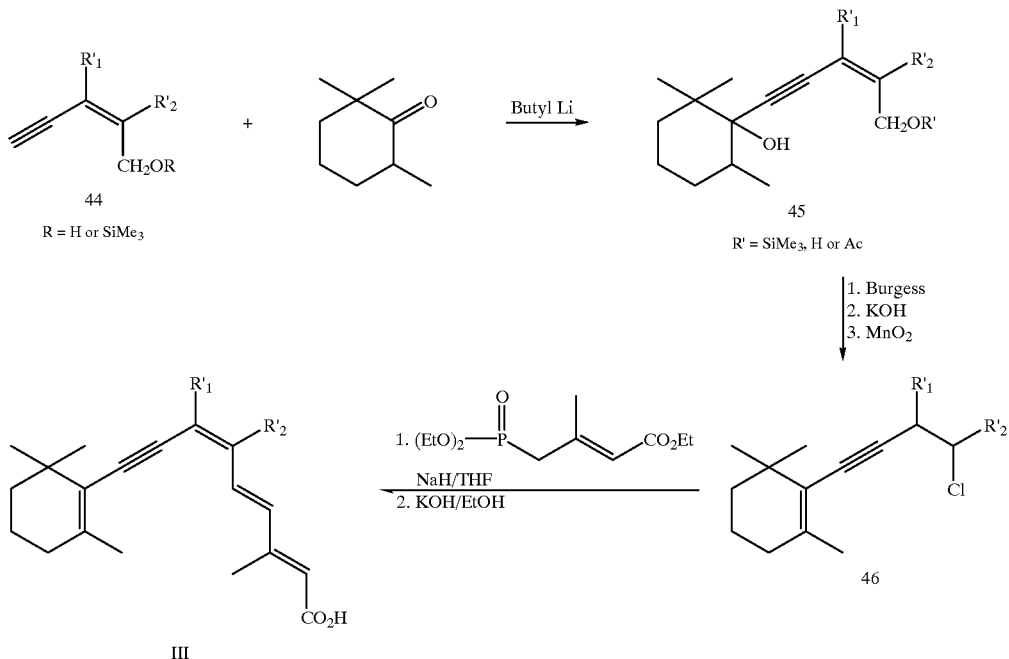

Schemes 1a–1d show the preferred methods for preparing intermediate esters for use in obtaining the compounds of formula I in which $R_1$ and $R_2$ are not taken together to form a ring. Scheme 1a is a route to compounds of formula I in which $R_1$ and $R_2$ are independently lower-alkyl. Scheme 1b is a route to compounds of formula I in which $R_1$ is lower-alkyl and $R_2$ is halogen or lower-alkyl. Scheme 1c is a route to compounds of formula I in which $R_1$ is lower-alkyl or halogen and $R_2$ is lower-alkyl, fluorine or chlorine. Scheme 1d is another route to compounds of formula I in which $R_1$ is lower-alkyl or halogen and $R_2$ is bromine. However, when $R_1$ is alkyl, the compounds of formula I where $R_2$ is bromine are preferably prepared via the route of Scheme 1b.

In Scheme 1a, exposure of 1 to strong base (e.g., lithium diisopropylamide) and alkylation of the enolate with an alkyl halide results in the formation of ester 3 which after exposure to base under equilibrating conditions (e.g., sodium ethoxide in refluxing ethanol) yields the ester 3 as predominantly one isomer (Z).

Scheme 1b is preferably used to obtain compounds of formula I where $R^2$ is halogen. However, Scheme 1b may also be used for the preparation of compounds of formula I in which $R_2$ is lower-alkyl. The addition of the cuprate $(R_1)_2LiCu$ to the acetylene 7 (Carotenoids, Otto Isled, ed. (Birkhauser Verlage, Basel, 1971)) yields the new cuprate from syn addition which on quenching with a suitable halide (e.g., iodine in dioxane) yields 3'; $R_2$=I. Quenching the cuprate with an alkyl halide will result in the ester 3' where $R_2$ is alkyl. The advantage of the cuprate chemistry is in the formation of a single isomer in most cases.

Scheme 1c is preferably used to obtain compounds of formula I where $R^2$ is lower-alkyl. Commercially available starting materials; e.g., β-ionone 14 ($R_{12}$=$CH_3$) are coupled with a suitable phosphonate 15 (Carotenoids, supra) to obtain the desired ester 3".

Scheme 1d may be used to form compounds of formula I where $R_2$ is bromine (G. Kobrich et al., *Llebigs Ann. Chem.*, 51:704 (1967)). The ketone 14 is converted to the alkene 16 by the referenced method. The known mixture of bromo acids 16 is converted to the mixture of esters 3''' (e.g., $R_1$=Me; $R_2$=Br) which are then separated by HPLC and then transformed into the final products as before.

With the esters 3, 3', 3", or 3''' in hand the final products are prepared through standard procedures (Carotenoids, supra). For example, the reaction may be carried out as shown in Scheme 2. In Scheme 2, reduction of any of the esters 3, 3', 3", or 3''' to the alcohol followed by reoxidation with manganese dioxide leads to the aldehyde 4. The aldehyde 4 is then coupled with the phosphonate 5 to yield the final product as the methyl ester 6. Base hydrolysis of 6 produces the free acid.

The compounds of formula I in which $R_1$ and $R_2$ taken together are $C_{3-13}$-alkylene are readily prepared as shown in Scheme 3 (R. M. Coates et al. *J.Org.Chem.*, 47:3597 (1982)). Thus, the cyclic ketone 8 (e.g., cyclopentanone or cyclohexanone, etc.) is exposed to phosphorus tribromide in dimethylformamide to give the bromoaldehyde 9 (Coates et al., supra) which is then coupled with the phosphonium salt $10^1$ to give the vinyl bromide 11. This vinyl bromide is then converted to the aldehyde 12 via transmetalation and reaction with dimethylformamide. With the new aldehyde in hand, the final product 13 is readily formed by coupling 12 with phosphonate 5. Hydrolysis then furnishes the desired acid.

Scheme 7 shows the prefered method for the preparation of intermediate 12 for use in Scheme 3, wherein $R^1$ and $R^2$ taken together are $C_{3-13}$-alkylene. Thus the ketone 8 is converted to the ester 36 by known methods (e.g., *Org. Synthesis*, Coll Vol. 5:198 (1973)) and then transformed into the enolphosphate 37. Displacement of the phosphate group with dimethyl cuprate (*J. Org. Chem.*, 53: 2984 (1988)) then gives the ester 38. Exposure of 38 to lithium diisopropylamide followed by the addition of cyclocitral 39 gives the lactone 40 (*Tet. Letters*, 21:2509 (1980)). Treatment of the lactone 40 with potassium t-butoxide and subsequently quenching the reaction product with methyl iodide yields the ester 41. Reduction with diisobutylaluminium hydride followed by subsequent oxidation with manganese dioxide then yields the aldehyde 12.

The routes shown in Schemes 4, 5 and 6 may be employed to obtain the compounds of formula I in which $R_1$ and $R_2$ taken together with the carbon atoms to which they are attached are 5–6 membered aromatic rings (e.g., thiophene, benzene, pyridine, etc.). Thus, in Scheme 4, a route to the benzene-containing structure 22 is shown. Phthalide is treated with triphenylphosphine hydrobromide and the resulting salt 17 is then coupled with the aldehyde 18 to give the acid ester 19 as shown. Reduction of the acid ester 19 via the acid chloride (not shown) yields the benzyl alcohol 20 which is then converted to the aldehyde 21, and then coupled with the cyclogeranylphosphonium ylide 10 to give the ester 22 which yields the acid after hydrolysis.

The various thiophene derivatives are prepared from a suitable bromothiophene as shown in Schemes 5 and 6. For example, in Scheme 5, 2,3-dibromothiophene 23 is selectively metalated and exposed to dimethylformamide to give the aldehyde 24 which is then homologated to the ester 25 with triethylphosphonoacetate. Reduction of the ester group gives the alcohol 26 which is protected as the acetal 27 which now allows one to again metalate and quench with dimethylformamide to yield the aldehyde 28. Condensation of 28 with the cyclogeranyalphosphonium ylide followed by acid treatment gives the alcohol 29. The alcohol 29 is then oxidised to the aldehyde 30 with manganese dioxide, exposed to methyl lithium and again oxidised with manganese dioxide to furnish the methyl ketone 31. Chain extension with triethyl phosphonoacetate then gives the desired material as the ester 32 which yields the acid on hydrolysis. Other analogs can be prepared in a similar fashion (see examples).

In Scheme 6, aldehyde 24 is coupled with the cyclogeranylphosphonium ylide 10 to give 33 which is selectively metalated and exposed to dimethylformamide to give the aldehyde 34. Chain extension with triethyl phosphonoacetate then gives the desired material as the ester 35, which yields the acid on hydrolysis.

Schemes 8 and 9 show the preferred methods for preparing compounds of formula I wherein the $C_7$–$C_8$ bond is a triple bond.

In Scheme 8, the aldehyde 42 is coupled in a Wittig-Horner reaction with 4-(diethoxy-phosphonyl)-3-methyl-but-2-enoic acid ethyl ester in the presence of a base, e.g. NaH, to give the ester 43.

2,2,6-Trimethylcyclohexanone is reacted with trimethylsilylacetylene (TMS-acetylene) using a strong base, e.g. butyl lithium. Elimination of water with Burgess-reagent (methoxycarbonylsulfamoyl-triethylammonium hydroxide, inner salt) and removal of the silyl protecting group with tetrabutylammonium fluoride leads to 2-ethynyl-1,3,3-trimethyl-1-cyclohexene.

This cyclohexene derivative is coupled with the ester 43 using the Pd $(Ph_3P)_4$/CuI complex as catalyst and piperidine as solvent. The resulting ester is then hydrolysed to the acid III.

In Scheme 9, 2-ethynyl-benzyl alcohol (compound 44, wherein R is H) is reacted with trimethylsilyl chloride. The protected alcohol (44, R=SiMe3) is reacted with 2,2,6-trimethyl-cyclohexanone after deprotonation with butyl lithium, to form the adduct 45 wherein R'is $SiMe_3$. Removal of the silyl protecting group with a base, e.g. aqueous potassium hydroxide, followed by acetylation with acetyl chloride and triethylamine leads to the acetate 45 (R'= acetyl).

Water is eliminated from the cyclohexanol derivative 45 by treatment with Burgess reagent to give the corresponding cyclohexene derivative. This is followed by hydrolysis of the acetyl group and oxidation with $MnO_2$ of the primary alcohol to give the aldehyde 46. The aldehyde 46 is reacted with 4-(diethoxy-phosphonyl)-3-methyl-but-2-enoic acid ethyl ester in a Wittig-Horner reaction to give the acid III after hydrolysis of its corresponding ester.

The following examples illustrate the invention. In the examples, concentration involves evaporation of the solvent employing a rotary evaporator at 40° C. and 20 mm Hg vacuum. HPLC refers to high performance liquid chromatography employing a Waters Prep 500 with silica cartridges. All intermediates and final products were characterized by HNMR spectroscopy.

EXAMPLE 1

Preparation of (2E,4E,6Z,8E)-3,6,7-Trimethyl-9-(2,6,6-trimethyl-1-cyclohexen-1-yl)-2,4,6,8-nonatetraenoic acid (All-E)-Ethyl-3-methyl-5-(2,6,6-trimethyl-1-cyclohexen-1-yl)-2,4-pentadienoate (1; Ri=Me; 13.1 g) was dissolved in tetrahydrofuran (25 ml) and then added to a freshly prepared solution of lithium diisopropylamide (1.2 equivalents with respect to the starting ester from diisopropyl amine and n-butyllithium; 1.6M in hexanes) dissolved in tetrahydrofuran (100 ml) at –70° C. The resulting solution was stirred a further 1hr. at this temperature and then treated with methyl iodide (10 ml) and allowed to warm to room temperature. Saturated aqueous ammonium chloride was added and the organic materials were isolated by extraction with a hexane/ ethylacetate mixture (4:1). Removal of the solvents in vacuo gave the alkylated product (14 g) as an oil. This material was dissolved in methanol (100 ml) containing sodium methoxide (10 ml; 4.6M in methanol) and heated at reflux for 2 hours. After this time the mixture was cooled to room temperature, treated with water and extracted with hexane/ ethylacetate as above. Removal of the solvents in vacuo gave crude methyl-(2Z,4E)-2,3-dimethyl-5-(2,6,6-trimethyl-1-cyclohexen-1-yl)-2,4-pentadienoate (13.2 g) as a 9:1 mixture of isomers about the 2,3 double bond. This material was dissolved in hexane (150 ml) cooled to –70° C. and then treated with an excess of diisobutylaluminum hydride (1M in hexane) and warmed to 0° C. Diethyl ether (200 ml) was then added followed by an aqueous solution of Rochelle salt (20%; 20 ml). The mixture was then carefully warmed to room temperature when a slight exothermic reaction set in. The mixture was allowed to heat to 35° C. and then cooled to room temperature. Solid magnesium sulphate (50 g) was then added and the solids were filtered off.

Removal of the solvents in vacuo gave the crude alcohol as an oil. This material was dissolved in hexane (20 ml) and added to a slurry of manganese dioxide (102 g) in a mixture of hexane-ether (1:1; 400 ml) cooled to 5° C. and stirred for 1.5 hours at this temperature and then for a further 1 hour at room temperature. The solids were then filtered off and the solution was concentrated in vacuo. Chromatography of the residue by HPLC (5% ether-hexane solvent system) gave pure (2Z,4E)-2,3-dimethyl-5-(2,6,6-trimethyl-1-cyclohexen-1-yl)-2,4-pentadienal (6 g; 51% overall yield from the ethyl ester).

Sodium hydride (1.3 g; 64% in oil) was washed with hexane, dried in vacuo and then suspended in tetrahydrofuran (60 ml) at 5° C. A solution of methyl 3-methyl-4-diethylphosphonocrotonate in tetrahydrofuran (8.6 g in 30 ml) was then added to the above suspension to yield a clear solution of the sodium salt (note: if turbid, the mixture is filtered through CELITE diatomateous earth). The clear solution was then cooled to 10° C. and treated with the above aldehyde (6 g) dissolved in tetrahydrofuran (20 ml) and then stirred at room temperature for 30 minutes. Hexane was then added and the mixture was washed with water, dried (magnesium sulphate), filtered free of solids and concentrated. Crystallization of the residue from hexane yielded pure methyl (2E,4E,6Z,8E)-3,6,7-Trimethyl-9-(2,6,6-trimethyl-1-cyclohexen-1-yl)-2,4,6,8-nonatetraenoate as a yellow crystalline solid. This material was dissolved in a mixture of ethanol-water (100 ml; 9:1) containing potassium hydroxide (4 g) and heated at reflux for 20 minutes. The mixture was then cooled to room temperature, poured into cold aqueous phosphoric acid (2M) and the solids were extracted into dichloromethane. Removal of the solvents in vacuo and crystallization of the residue from acetonitrile gave (2E,4E,6Z,8E)-3,6,7-Trimethyl-9-(2,6,6-trimethyl-1-cyclohexen-1-yl)-2,4,6,8-nonatetraenoic acid (3.8 g) as a pale yellow colored crystalline solid. This material showed the characteristic peaks in the proton magnetic resonance spectrum for the E,E,Z,E polyene system.

EXAMPLE 2

Preparation of (All-E)-6-Bromo-3,7-dimethyl-9-(2,6,6-trimethyl-1-cyclohexen-1-yl)-2,4,6,8-nonatetraenoic acid A mixture of (2E,4E) and (2Z,4E)-2-bromo-3-methyl-5-(2,6,6-trimethyl-1-cyclohexen-1-yl)-2,4-pentadienoic acid (75 g) was dissolved in dimethylformamide (500 ml) and slowly added to a suspension of sodium hydride (10.5 g; 65% in oil) in tetrahydrofuran (1100 ml) at 10° C. and then stirred until all hydrogen evolution ceased. Methyl iodide (50 g) was then added and the resulting mixture was heated for 2 hours at 50–60° C., poured onto an ice-water mixture and extracted with hexane. The hexane extracts were washed with water, dried (magnesium sulphate) and concentrated. The mixture of methyl esters was then separated by HPLC (2.5% ether/hexane) to give pure methyl (2Z,4E)-2-bromo-3-methyl-5-(2,6,6-trimethyl-1-cyclohexen-1-yl)-2,4-pentadienoate (20 g) and methyl (2E,4E)-2-bromo-3-methyl-5-(2,6,6-trimethyl-cyclohexen-1-yl)-2,4-pentadienoate (37 g).

The (2E,4E)-2-bromo-3-methyl-5-(2,6,6-trimethyl-1-cyclohexen-1-yl)-2,4-pentadienoate (37 g) was reduced to the alcohol as in Example 1 and then immediately exposed to manganese dioxide to give the unstable aldehyde (15 g). This material was then converted to ethyl (All-E)-6-bromo-3,7-dimethyl-9-(2,6,6-trimethyl-1-cyclohexen-1-yl)-2,4,6,8-nonatetraenoate and subsequently hydrolyzed to (All-E)-6-Bromo-3,7-dimethyl-9-(2,6,6-trimethyl-1-cyclohexen-1-yl)-2,4,6,8-nonatetraenoic acid, as in Example 1.

EXAMPLE 3

Preparation of (All-E)-6-Iodo-3,7-dimethyl-9-(2,6,6-trimethyl-cyclohexen-1-yl)-2,4,6,8-nonatetraenoic acid A slurry of cuprous bromide dimethylsulfide complex (10.3 g) in tetrahydrofuran (500 ml) at 0° C. was treated with a solution of methyl lithium in ether (1.4M; low bromide), stirred a further 15 minutes and then cooled to −70° C. To this cold clear solution was added ethyl (E)-5-(2,6,6-trimethyl-1-cyclohexen-1-yl)-4-penten-2-ynoate (10 g) dissolved in tetrahydrofuran (50 ml) and the mixture was stirred for 2 hours and then treated with a solution of iodine in tetrahydrofuran (13 g in 100 ml) over 0.5 hours. After this period, the mixture was warmed to −60° C. and poured into aqueous ammonium chloride solution, and the organic materials were extracted into hexane. The hexane extracts were washed with dilute aqueous sodium thiosulphate solution, dried (sodium sulphate), and concentrated at room temperature to yield the unstable iodoester which was purified by HPLC (2.5% ether/hexane) giving pure ethyl (2E,4E)-2-iodo-3-methyl-5-(2,6,6-trimethyl-1-cyclohexen-1-yl)-2,4-pentadienoate (5 g). This ester was transformed into the corresponding aldehyde and was then coupled with the phosphonate as in previous examples, and the resulting retinoic acid ester analog was hydrolyzed to yield the pure (All-E)-6-iodo-3,7-dimethyl-9-(2,6,6-trimethyl-1-cyclohexen-1-yl)-2,4,6,8-nonatetraenoic acid as a pale yellow solid after crystallization from a hexane/tetrahydrofuran mixture.

EXAMPLE 4

Preparation of (2E,4E)-3-Methyl-5-(2-((E)-2(2,6,6-trimethyl-1-cyclohexen-1-yl)ethenyl)-1-cyclohexen-1-yl)-2,4-pentadienoic acid A suspension of ((2,6,6-trimethyl-1-cyclohexen-1-yl)methyl)triphenylphosphonium chloride (18 g) in tetrahydrofuran (300 ml) was cooled to −60° C., treated dropwise with n-butyllithium (1.4M in hexane; 32 ml), and then stirred a further 10 minutes. To this cold solution was added the 2-bromocyclohexene-1-carboxaldehyde (8.5 g,75% pure by HNMR analysis) dissolved in tetrahydrofuran, and the mixture was allowed to warm to room temperature after which it was stirred for a further 2 hours. Hexane was then added to the reaction and the resulting mixture was washed with water, 50% aqueous methanol and dried (magnesium sulphate). Removal of the solvents yielded the crude (E)-1-bromo-2-(2-(2,6,6-trimethyl-1-cyclohexen-1-yl)ethenyl)-cyclohexene (12.5 g) as a mixture of isomers which was used, as is, in the next step. Standard transmetalation and reaction with DMF yielded a cruce aldehyde (4.5 g) which was dissolved in tetrahydrofuran (100 ml) and reacted with an excess of the phosphonate as in Example 1to give methyl (2E,4E)-3-methyl-5-(2-((E)-2(2,6,6-trimethyl-cyclohexen-1-yl)ethenyl)-1-cyclohexen-1-yl)-2,4-pentadienoate (3 g) as an oil after purification by HPLC (2.5% ether in hexane). Hydrolysis with aqueous potassium hydroxide solution gave crystalline (2E,4E)-3-Methyl-5-(2-((E)-2(2,6,6-trimethyl-cyclohexen-1-yl)ethenyl)-1-cyclohexen-1-yl)-2,4-pentadienoic acid (1.6 g from hexane-tetrahydrofuran).

EXAMPLE 5

Preparation of (2E,4E)-3-Methyl-5-(2-((E)-2(2,6,6-trimethyl-1-cyclohexen-1-yl)ethenyl)-1-cyclopenten-1-yl)-2,4-pentadienoic acid As in Example 4, 2-bromocyclopentene-1-carboxaldehyde was converted to (2E,4E)-3 Methyl-5-(2-((E)-2(2,6,6-trimethyl-1-cyclohexen-1-yl)ethenyl)-1-cyclopenten-1-yl)-2,4-pentadienoic acid ethyl ester which on hydrolysis with base gave (2E,4E)-3-Methyl-5-(2-((E)-$^2$(2,6,6-trimethyl-1-cyclohexen-1-yl)ethenyl)-1-cyclopenten-1-yl)-2,4-pentadienoic acid.

EXAMPLE 6

Preparation of (2E,4E)-3-Methyl-5-(2-((E)-2(2,6,6-trimethyl-1-cyclohexen-1-yl)ethenyl)-1-cyclohepten-1-yl)-2,4-pentadienoic acid As in Examples 4 and 5, 1-bromocycloheptene-2-carboxaldehyde was converted to (2E,4E)-3-Methyl-5-(2-

((E)-2(2,6,6-trimethyl-1-cyclohexen-1-yl)ethenyl)-1-cyclohepten-1-yl)-2,4-pentadienoic acid ethyl ester which gave (2E,4E)-3-Methyl-5-(2-((E)-2(2,6,6-trimethyl-1-cyclohexen-1-yl)ethenyl)-1-cyclohepten-1-yl)-2,4-pentadienoic acid after hydrolysis with base.

EXAMPLE 7

Preparation of (2E,4E)-3-Methyl-5-(2-((E)-2(2,6,6-trimethyl-1-cyclohexen-1-yl)ethenyl)-1-cyclooc ten-1-yl)-2,4-pentadienoic acid As in the above Examples, 1-bromocyclooctene-2-carboxaldehyde was converted into (2E,4E)-3-Methyl-5-(2-((E)-2(2,6,6-trimethyl-1-cyclohexen-1-yl)ethenyl)-1-cycloocten-1-yl)-2,4-pentadienoic acid ethyl ester and subsequently into (2E,4E)-3-Methyl-5-(2-((E)-2(2,6,6-trimethyl-1-cyclohexen-1-yl)ethenyl)-1-cycloocten-1-yl)-2,4-pentadienoic acid by base hydrolysis.

EXAMPLE 8

Preparation of (2E,4E)-3-methyl-5-(2-(2-((E)-2-(2,6,6-trimethyl-1-cyclohehex-1-yl) ethenyl)-1-phenyl)-2,4-pentadienoic acid As shown in Scheme 4, phthalide (0.1 Mol) and triphenylphosphine hydrobromide (0.1 Mol) were heated at 200° C. for two hours, cooled to room temperature and then digested with hot acetonitrile to yield the salt 17 (39 g) as a white solid. A solution of this salt (4.6 g) in dimethylsulphoxide (DMSO; 50 ml) at 5° C. was treated with a solution of the sodium salt of DMSO (IM; 20 ml) followed by the aldehyde 18 (1.5 g) to yield a pale yellow colored reaction mixture. Water was then added and the resulting mixture was acidified with aqueous phosphoric acid (2M) and the acid 19 was isolated by extraction into ethyl acetate. The crude product (4.3 g) was disolved in benzene and exposed to oxalyl chloride (3 ml) and dimethylformamide (3 drops), and then held at room temperature for 30 minutes. Removal of the solvents in vacuo followed by disolution of the crude acid chloride in tetrahydrofuran (100 ml) yielded the alcohol 20 after the addition of sodium borohydride at −20° C. and warming to room temperature. Purification of the crude alcohol by HPLC followed by crystallization from a hexane/ethylacetate mixture gave 3-methyl-5-(2-hydroxymethylphenyl)-2,4-pentadienoic acid ethyl ester 20 as a colorless solid (1.1 g). Exposure of the alcohol 20 (1.1 g) to a slurry of manganese dioxide (11 g) in hexane/dichloromethane (5:1; 60 ml) at 0° C. followed by stirring for a further 2 hours at room temperature gave the aldehyde 21 (1.1 g). A solution of the phosphonium ylide derived from cyclogeranylphosphonium bromide 10 (1.3 g) in tetrahydrofuran (20 ml) and n-butyllithium at 10° C. was then treated with the crude aldehyde 21 (1.0 g) and warmed to room temperature over 15–30 minutes. Dilution with water and extraction of the organic materials in to a hexane/ethylacetate mixture (4:1) gave the crude adduct 22 as an oil. This material in hexane was passed through a plug of silicagel to yield the ester (0.8 g) as an oil. Hydrolysis of this material with aqueous potassium hydroxide in refluxing ethanol yielded the acid after acidification with mineral acid (2M phosphoric acid). Crystallization from a hexane/ethylacetate mixture gave the pure (2E,4E)-3-methyl-5-(2-(2-((E)-2-(2,6,6-trimethyl-1-cyclohehex-I -yl) ethenyl)-1-phenyl)-2,4-pentadienoic acid as a white solid.

EXAMPLE 9

Preparation of (2E,4E)-3-Methyl-5-(3-((E)-2-(2,6,6-trimethyl-1-cyclohexen-1-yl) ethenyl)-2-thienyl)-2,4-pentadienoic acid A solution of 2,3-dibromothiophene (0.1 mol) in diethyl ether (aproximately 5% concentration) was treated with n-butyllithium (1.6M in hexane; 1.1equivalents) at −70° C. and stirred for 30 minutes. Excess dimethylformamide was then added and the mixture was warmed to room temperature, quenched with water, and then acidified with dilute aqueous phosphoric acid. Extraction with hexane gave the crude aldehyde which was then purified by HPLC. The total aldehyde from this run was then added to an excess of the sodium salt of triethylphosphonoacetate in tetrahydrofuran and the mixture was stirred at room temperature for 1 hour and then quenched with water and acetic acid. The crude ester 25 was then added to an excess of diisobutylaluminum hydride in hexane at −40° C. and the mixture was then warmed to 0° C. and quenched with an aqueous solution of Rochelle salt (20%; 10 ml) and warmed to 32° C. Extraction with hexane then gave the alcohol 26 which was converted to the acetal 27 with 2-methoxypropene. After purification of the acetal by HPLC, the total product was disolved in tetrahydrofuran (≈5% concentration) cooled to −70° C. and then treated with n-butyllithium as before. After stirring a further 30 minutes at this temperature, an excess of dimethylformamide was added and the mixture was warmed to room temperature and quenched with aqueous ammonium chloride soution (20%) to give the aldehyde 28 after isolation with hexane and purification by HPLC. This aldehyde was then exposed to an excess (1.2 equiv.) of the ylide formed from cyclogeranylphosphonium bromide 10 and n-butyllithium in tetrahydrofuran and hexane at −70° C. and then stirred a further 2 hours at room temperature. Addition of water and dilute aqueous phosphoric acid then yielded the alcohol 29 after extraction into hexane. This material was dissolved in diethyl ether (min. volume) and then added to a slurry of manganese dioxide (10 fold) in more ether (300 ml) at 0° C. and the warmed to room temperature. After stirring for a further 1 hour, the solids were filtered off and removal of the solvent gave the aldehyde 30 after purification by HPLC. This material was then dissolved in ether, cooled to −10° C. and exposed to an excess of methyl lithium in ether (1.4 equiv.) and subsequently warmed to room temperature. Addition of water and concentration of the organic phase gave the crude alcohol which was oxidised with manganese dioxide, as above, yielding the ketone 31. Exposure of this material to an excess of the sodium salt of triethylphosphonoacetate in tetrahydrofuran at room temperature gave the desired ester 32 (R=ethyl) as a mixture of isomers about the newly formed double bond (≈4:1) with the desired isomer predominating. Purification of this mixture by HPLC and crystallization of the major isomer from hexane gave the pure ethyl-(2E,4E)-3-Methyl-5-(3-((E)-2-(2,6,6-trimethyl-1-cyclohexen-1-yl) ethenyl)-2-thienyl)-2,4-pentadienoate. Hydrolysis with aqueous potassium hydroxide solution in refluxing ethanol as in Example 8 gave the pure (2E,4E)-3-Methyl-5-(3-((E)-2-(2,6,6-trimethyl-1-cyclohexen-1-yl) ethenyl)-2-thienyl)-2,4-pentadienoic acid after crystallization from a tetrahydrofuran/hexane mixture.

EXAMPLE 10

Preparation of (2E,4E)-3-Methyl-5-(2-((E)-2-(2,6,6-trimethyl-1-cyclohexen-1-yl) ethenyl)-3-thienyl)-2,4-pentadienoic acid As in Example 9, 2,3-dibromothiophene was converted into the aldehyde 24 and then exposed to the ylide derived from cyclogeranylphosphonium bromide10 and n-butyllithium to give the adduct 33. Treatment of the bromo compound 33 with n-butyllithium in hexane/tetrahydrofuran as in Example 9, followed by a excess of dimethylformamide, gave aldehyde 34 after workup with aqueous phosphoric acid. This material was then coupled with the phosphonate 5 as in Example 1 to give the methyl-(2E,4E)-3-methyl-5-(2-((E)-2-(2,6,6-trimethyl-1- cyclohexen-1-yl)ethenyl)-3-thienyl)-2,4-pentadienoate (R=methyl) as a mixrure of isomers about the terminal double bond. Purification by HPLC gave methyl-(2E,4E)-3-methyl-5-(2-((E)-2-(2,6,6-trimethyl-1-cyclohexen-1-yl) ethenyl)-3-thienyl)-2,4-pentadienoate which after hydrolysis as above gave the pure (2E,4E)-3-methyl-5-(2-((E)-2-(2, 6,6-trimethyl-1-cyclohexen-1-yl) ethenyl)-3-thienyl)-2,4-pentadienoic acid on crystallization from a tetrahydrofuran/hexane mixture.

EXAMPLE 11

Preparation of (2E,4E)-3-methyl-5-(4-((E)-2-(2,6,6-trimethyl-1-cyclohexen-1-yl)ethenyl)-3-thienyl)-2,4-pentadienoic acid Treatment of 3,4-dibromothiophene as in Example 10 gives (2E,4E)-3-Methyl-5-(4-((E)-2-(2,6,6-trimethyl-1-cyclohexen-1-yl)ethenyl)-3-thienyl)-2,4-pentadienoic acid.

EXAMPLE 12

Preparation of (All-E-)-6-chloro-3,7-dimethyl-9-(2, 6,6-trimethyl-1-cyclohexen-1-yl)-2,4,6,8-nonatetraenoic acid A solution of triethyl 2-chlorophosphono acetate (*J. Org. Chem.*, 51:5467 (1986)) (0.12M) in tetrahydrofuran was treated with sodium hydride (64% oil suspension; 0.12M) and stirred at room temperature to give a clear solution of the anion. To this mixture was added 6-ionone (0.1M) and the reaction was heated at 45° C. overnight. Water was then added and the products were extracted into hexane/ethylacetate (4:1). Removal of the solvents yielded the coupled product as a mixture (1:1) of double bond isomers from which the desired isomer, ethyl-(2E,4E)-2-chloro-3-methyl-5-(2,6,6-trimethyl-1-cylohexen-1-yl)-2,4-pentadienoate, was separated by HPLC. Reduction of this ester with diisobutyaluminum hydride as in Example 1, followed by oxidation with manganese dioxide as before, gave (2E,4E)-2-chloro-3-methyl-5-(2,6,6-trimethyl-1-cyclohexen-1-yl)-2,4-pentadienal. This material was then coupled with methyl 3-methyl-4-diethylphosphonocrotonate as in Example 1 to give methyl (all-E)-6-chloro-3,7-dimethyl-9-(2,6,6-trimethyl-1-cyclohexen-1-yl)-2,4,6,8-nonatetraenoate. Hydrolysis of the ester as before, and crystallization of the acid from a mixture of tetrahydrofuran and hexane, yielded pure (all-E)-6-chloro-3,7-dimethyl-9-(2,6,6-trimethyl-1-cyclohexen-yl)-2,4,6,8-nonatetraenoic acid as a yellow colored solid.

EXAMPLE 13

Preparation of All-E-3,7-Dimethyl-9-[(2-methoxy-4-methyl-6-octyloxy)phenyl]-2,4,6,8-nonatetraenoic acid A solution of 2,6-dihydroxy-4-methyl-benzoic acid in acetone (50.4 g; 750 ml) was treated with methyl iodide (100 ml) and potassium carbonate (124.2 g) and heated at reflux for 18 hours. The mixture was then cooled to room temperature and filtered free of solids. Concentration of the solution gave the crude product which was dissolved in ethylacetate and washed with aqueous sodium hydroxide solution (IN; cold). Removal of the solvents in vacuo then gave methyl 2,6-dimethoxy-4-methyl-benzoate (54 g). This material (52.5 g) was dissolved in dichloromethane (1000 ml) cooled to −70° and treated with a solution of borontrichloride in the same solvent (29.3 g/100 ml; 180 ml). This mixture was then warmed up to room temperature and stirred for a further 45 minutes and then poured onto ice. The organic layer was separated, washed with more water, dried (magnesium sulphate), filtered and concentrated.

The residue was then purified by high performance preparative liquid chromatography (HPLC) using a Waters prep.500 chromatograph (7% ethyl acetate/hexane eluent) to give pure methyl 2-hydroxy-6-methoxy-4-methyl benzoate as a solid (28.3 g). A solution of this material (35 g) in methyl ethyl ketone (700 ml) containing potassium carbonate (27.1 g) was treated with 1-octyliodide (34.2 g) and heated at reflux for 20 hours. The reaction mixture was cooled filtered free of solids and the filterate was concentrated and then redisolved in a mixture of hexane and ethyl acetate. This solution was then washed with aqueous base (IN sodium hydroxide), water, dried (magnesium sulphate) and concentrated to dryness. Puification by HPLC as before gave pure methyl 2-methoxy-6-octyloxy-4-methyl-benzoate (51.8 g).

A solution of this material (51.8 g) in toluene (500 ml) was cooled to −60° and treated with a solution of diisobutyaluminum hydride (25% in hexane; 281 ml) and then warmed to room temperature. The reaction mixture was then carefully treated with aqueous methanol (100 ml; 1:1) with cooling so that the temperature was kept at 20° followed by the addition of hexane (500 ml) and magnesium sulphate. The solids were then filtered off and the solvents were removed in vacuo to yield the crude alcohol. This material (47 g) was disolved in acetonitrile (500 ml) containing triphenylphosphonium hydrobromide (54.9 g) and heated at reflux for 22 hours. The solvents were then removed in vacuo and the crude salt was dried at room temperature at 0.1 mm pressure (this material can be crystallised from tetrahydrofuran to give pure [(2-methoxy-6-Octyloxy-4-methyl)phenyl]methyl-triphenylphosphonium bromide). This salt was then converted into All-E-3,7-Dimethyl-9-[(2-methoxy-4-methyl-6-octyloxy)phenyl]-2,4,6,8-nonatetraenoic acid as described in U.S. Pat. No. 4,894,480, Example 5.

EXAMPLE 14

Preparation of (E)-2-(2-(2,6,6-trimethyl-1-cyclohexen-1-yl)ethenyl)-cycloheptene carboxaldehyde As shown in Scheme 7, cycloheptanone (152 g) was converted to the ester (Org.Syn. Coll., 5: 198 (1973); 232 g), transformed into the enolphosphate 37 (274 g) and subsequently treated with lithium dimethylcuprate to yield ethyl-2-methyl-cyclohept-1-eneoate 38 (119 g). A solution of ethyl-2-methyl-cyclohept-1-eneoate (91 g) in tetrahydrofuran was then added to a solution of lithium diisopropylamide (0.53 Mol) and then quenched with cyclocitral 39 (76 g) to yield the lactone 40 (113 g) after acid work up. Exposure of 40 to potassium tertiarybutoxide in tetrahydrofuran followed by an excess of methyl iodide gave the methyl ester 41 (111 g). Reduction of the above ester with diisobutylaluminium hydride followed by oxidation with manganese dioxide as in Example 1 furnished the aldehyde 12 (n=3)(98 g).

EXAMPLE 15

A: Preparation of (2E, 4E)-3-Methyl-5-(2,6,6-trimethyl-cyclohex-1-enylethynyl)-cyclopent-1-enyll-penta-2,4-dienoic acid ethyl ester (2E,4E)-5-(2-Bromo-cyclopent-1-enyl)3-methyl-penta-2, 4-dienoic acid ethyl ester (1.43 g) was dissolved in 5 ml of benzene. At ambient temperature was added successively: 293 mg of Pd(Ph$_3$P)$_4$, 95 mg of CuI, 147 mg of (Ph)$_3$P, and 8 ml of piperidine. To this mixture was added via dropping funnel within 1 hour 2-ethynyl-1,3,3-trimethyl-1-cyclohexene (745 mg) dissolved in 5 ml of benzene. After 4.5 hours, additional acetylene (350 mg) was added and stirring continued for 30 minutes. The mixture was then poured into crushed ice/HCl, extracted with EtOEt, washed twice with water, dried over $Na_2SO_4$, and evaporated to dryness. Medium pressure chromatography ($SiO_2$, hexane/AcOEt=98/2) yielded 1.478 g of (2E, 4E)-3-Methyl-5-(2,6,6-trimethyl-cyclohex-1-enylethynyl)-cyclopent-1-enyl]-penta-2,4-dienoic acid ethyl ester as a yellow oil.

The prerequisite (2E,4E)-5-(2-bromo-cyclopent-1-enyl)-3-methyl-penta-2,4-dienoic acid ethyl ester was synthesized as follows:

2.03 g of NaH (50% in mineral oil) was suspended in 120 ml of DMF. 4-(Diethoxy-phosphinyl-3-methyl-but-2-enoic acid ethyl ester (12.9 g) was added at 0° C. The mixture was stirred for 15 minutes at 0° C. and for 30 minutes at RT. After recooling to 0° C., 2-bromo-cyclopent-1-ene-carbaldehyde (5.72 g), dissolved in 11 ml of DMF, was added drop by drop and allowed to react for 10 minutes at 0° C. and for 2 hours at RT. The mixture was then poured into crashed ice. extracted with EtOEt, washed with sat. NaCl-solution, dried over $Na_2SO_4$, and evaporated to dryness. Purification of the residue by flash chromatography (silica gel, hexane/AcOEt= 97/3) and crystallization from hexane/trace amounts of AcOEt yielded finally 3.408 g of pure (2E,4E)-5-(2-bromo-cyclopent-1-enyl)-3-methyl-penta-2,4-dienoic acid ethyl ester as yellowish crystals of mp. 85–86° C.

The prerequisite 2-ethynyl-1,3,3-trimethyl-1-cyclohexene was synthesized according to standard procedures by addition of the Li-derivative of TMS-acetylene to 2,2,6-trimethylcyclohexanone, dehydration by treatment with Burgess-reagent (methoxy-carbonylsulfamoyl-triethylammonium hydroxide, inner salt), and finally desilyation with tetrabutylammonium fluoride. It has to be used immediately due to its instability.

B: Preparation of (2E,4E)-3-Methyl-5-[2-(2,6,6-trimethyl-cyclohex-1-enylethynyl)-cyclopent-1-enyl]-penta-2,4-dienoic acid (2E,4E)-3-Methyl-5-[2-(2,6,6-trimethyl-cyclohex-1-enylethynyl)-cyclopent-1-enyl]-penta-2,4-dienoic acid ethyl ester (1. 47 g) was dissolved in 14 ml of THF/EtOH=1/1. 3N aqueous NaOH (7.0 ml) was added and the reaction flask kept in the dark. After stirring for 16 hours at ambient temperature, the mixture was poured onto crushed ice/HCl, extracted twice with EtOEt, washed with water, dried over $Na_2SO_4$, and evaporated to dryness. Crystallization from EtOEt/pentane afforded 1.31 g of (2E,4E)-3-Methyl-5-[2-(2,6,6-trimethyl-cyclohex-1-enylethynyl)-cyclopent-1-enyl] -penta-2,4-dienoic acid as yellow crystals of mp. 173–174° C.

EXAMPLE 16

In analogy to Example 15 was prepared:
(2E,4E)-3-Methyl-5-[2-(2,6,6-trimethyl-cyclohex-1-enylethynyl)-cyclohept-1-enyl]-penta-2,4-dienoic acid as yellow crystals of mp. 166–167° C.

EXAMPLE 17

Preparation of (2E,4E)-3-Methyl-5-[2-(2,6,6-trimethyl-cyclohex-1-enylethynyl)-phenyl]-penta-2, 4-dienoic acid 229 mg of (2E,4E)-3-Methyl-5-[2-2,6,6-trimethyl-cyclohex-1-enylethynyl)-phenyl]-penta-2,4-dienoic acid ethyl ester were dissolved in 8 ml of ethanol. After adding a solution of 411 mg of potassium hydroxide in 2.5 ml of water, the reaction mixture was stirred at 50° C. for 2 hours. The mixture was then poured onto ice/water, acidified with 2N hydrogen chloride and extracted with ethyl acetate. The organic phase was washed with water, dried over sodium sulfate and evaporated to give slightly yellow crystals which were recrystallized from ethyl acetate/hexane. Yield 93 mg of (2E,4E)-3-Methyl-5-[2-(2,6,6-trimethyl-cyclohex-1-enylethynyl)-phenyl]-penta-2,4-dienoic acid, m.p. 194–196° C.

The starting material used in this example was prepared as follows:

970 mg of 2-ethynyl-benzyl alcohol were dissolved in 50 ml of diethyl ester. 1.9 ml of triethylamine was added, followed by dropwise addition of 0.9 ml of trimethylsilyl chloride. The reaction mixture was stirred at room temperature for 4 hours, poured onto ice/5% aqueous sodium bicarbonate and extracted with ether. The oily residue obtained after drying and evaporation of the solvent was distilled to give 1.3 g of 2-ethynylbenzyl trimethylsilyl ether as a colourless oil, b.p. 85–89° C./0.8 mm.

This colourless oil was dissolved in 5 ml of tetrahydrofuran. After the dropwise addition of 3.9 ml of butyl lithium (1.6 molar in hexane) at −78° C., the reaction mixture was stirred at this temperature for 30 minutes. A solution of 0.59 g of 2,2,6-trimethyl-cyclohexanone in 4 ml of tetrahydrofuran was dropped in and the reaction mixture was stirred at room temperature for 5 hours, resulting in a yellow solution. The yellow solution was poured onto ice water/10% aqueous ammonium chloride, extracted with hexane, dried over sodium sulfate and evaporated. The yellow, oily residue was purified by flash chromatography ($SiO_2$, hexane/5 % ethyl acetate) to give 1.7 g of a yellow oil.

The yellow oil was dissolved in 90 ml of tetrahydrofuran and stirred for 6 hours at room temperature with 28.8 ml of a 0.5 normal aqueous solution of potassium hydroxide. The reaction mixture was poured onto ice/water, extracted with ether, washed with water, dried and evaporated. Purification of the residue by flash chromatography ($SiO_2$, hexane/ethyl acetate =7:3) and crystallization from ethyl acetate/hexane yielded 1.1 g of white crystals, m.p. 120–121° C.

The white crystals were dissolved in 10 ml of tetrahydrofuran and sequentially treated with 679 mg of triethylamine and 400 mg of acetylchloride. After 4 hours of stirring at room temperature, the reaction mixture was poured onto ice/1N hydrogen chloride, extracted with ether, dried over sodium sulfate and evaporated. Flash chromatography ($SiO_2$, hexane/ethyl acetate −4:1) yielded 0.8 of a colourless oil.

The colourless oil was dissolved in 13 ml of benzene and added to a solution of 1.3 g of Burgess-reagent (methoxycarbonylsulfamoyl-triethylammonium hydroxide, inner salt) in 40 ml of benzene. The reaction mixture was heated to 60° C. for 3 hours. After distilling off most of the solvent, the residue was dissolved in ice water and extracted with ether. The residue obtained after drying and evaporation of the solvent was purified by flash chromatography ($SiO_2$, hexane/ethyl acetate =9:1) to give 0.7 g of a slightly yellow oil.

This yellow oil was dissolved in 18 ml of ethanol and treated with a solution of 0.78 g of potassium hydroxide in 4 ml of water at 45° C. for 2.5 hours. The reaction mixture was poured onto ice/saturated ammonium chloride solution, extracted with ether, dried and evaporated. The residue was purified with medium pressure liquid chromatography ($SiO_2$, hexane/ethyl acetate =9:1) to give 0.46 g of a slightly yellow oil. This yellow oil was dissolved in 20 ml of methylene chloride and treated with 1.6 g qf manganese dioxide for 15 hours under vigorous stirring at room temperature. The manganese dioxide was filtered off, the filtrate evaporated and the residue purified with medium pressure chromatography ($Si)_2$, hexane/2% ethyl acetate) to give 225 mg of 2-(2,6,6-trimethyl-cyclohex-1-enylethynyl)-benzaldehyde as yellow oil which solidified in the cold.

85 mg of sodium hydride (50% in mineral oil) was washed with pentane and suspended in 4 ml of tetrahydrofuran. 470 mg of 4-(diethoxyphosphonyl)-3-methyl-but-2-enoic acid ethyl ester dissolved in 4 ml of tetrahydrofuran was added dropwise at 0° C., and the reaction mixture was stirred at room temperature for 1 hour. After recooling to 0° C., a solution of 225 mg of the yellow aldehyde from the previous step in 3 ml of tetrahydrofuran was dropped in. The reaction mixture was stirred at room temperature for 3 hours, poured onto ice/saturated ammonium chloride solution, extracted with ether, washed with water, dried and evaporated. The residue was purified first with flash chromatography ($SiO_2$, hexane/5% ethyl acetate) and then with medium pressure liquid chromatography ($SiO_2$, hexane/2% ethyl acetate) to give 229 mg of (2E,4E)-3-methyl-5-[2-(2,6,6-trimethyl-cyclohex-1 enylethynyl)-phenyl]-penta-2,4-dienoic acid ethyl ester as a colourless oil.

EXAMPLE 18

Under the influence of retinoids, HL-60 cells (a human myeloid leukemia cell line) differentiate into granulocytes. This differentiation of HL-60 cells into granulocytes is mediated by RARα, and so provides the basis for the use of retinoids to treat leukemia. The results of this test demonstrate that the RXR-selective compounds of the invention, at doses where they are inactive by themselves, are able to potentiate by up to an order of magnitude the pro-differentiating effects of all-trans retinoic acid and another RARα-selective retinoid having the following formula:

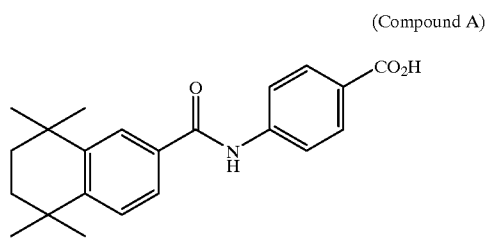

(Compound A)

The ability of the test compounds to transactivate the retinoid receptors are as follows:

TABLE 1

| | Activation ($ED_{50}$, nM) | |
|---|---|---|
| | RARα | RXRα |
| All-trans retinoic acid | 6.7 | 41 |
| Compound A | 3 | >10,000 |
| Example 4 | >10000 | 1.7 |

HL-60 Differentiation

Retinoid-induced differentiation of HL-60 cells was assayed by measuring their oxidative burst potential via the reduction of NBT (Nitroblueterstazolium) [Pick et al., *J. Reticuloendothelial Soc.*, 30:581–593 (1981)].

HL-60 cells were maintained in RPMI 1640 medium supplemented with 10% FCS, 2mM L-glutamine, ImM sodium pyruvate, 1% non-essential amino acids, 50 U/ml penicillin and 50 μg/ml streptomycin (=RPMI/FCS). The cells were found to be free of mycoplasma.

30,000 cells/100 1 of RPMI/FCS were seeded into flat-bottomed microtiter wells. 10 μl of retinoids diluted in complete medium were added at the same time to yield final concentrations betweeen $10^{-11}$ and $10^{-6}$M (stock solutions of $10^{-2}$M in ethanol were kep at –20° C. and protected from light). After 3 days, the medium was removed with a multichannel pipette and replaced with 100 μl of NBT solution (1 mg/ml in PBS with 200 nM phorbol myristate acetate (PMA). Following an additional hour incubation at 37° C. the NBT solution was removed and 100 μl of 10% SDS in 0.01 N HCl was added. The amount of the reduced NBT was quantified photometrically at 540 nm using an automated plate reader. The mean of 3 wells was calculated. S.E.M. were between 5 and 10%.

Results
Effects of RXR-selective retinoids on HL-60 differentiation

In agreement with its weak potency as an activator of RARα, the Example 4 RXR-selective retinoid was clearly less active as an inducer of HL-60 differentiation than all-trans retinoic acid (FIG. 1). Indeed, Example 4 was virtually inactive even at $\times 10^{-6}$ M, in good agreement with its transactivation characteristics. HL-60 cells appear to be about 10× more sensitive to retinoids than the transactivation system (compare Table 1, RARα and FIG. 1).

Figure 2:
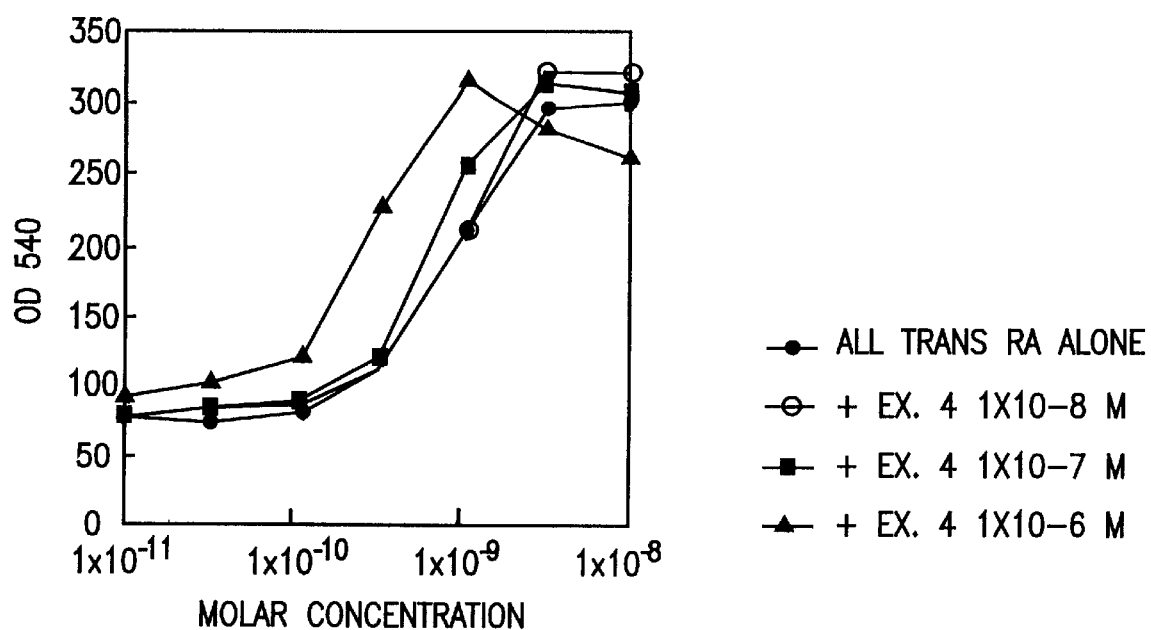
Figure 3:
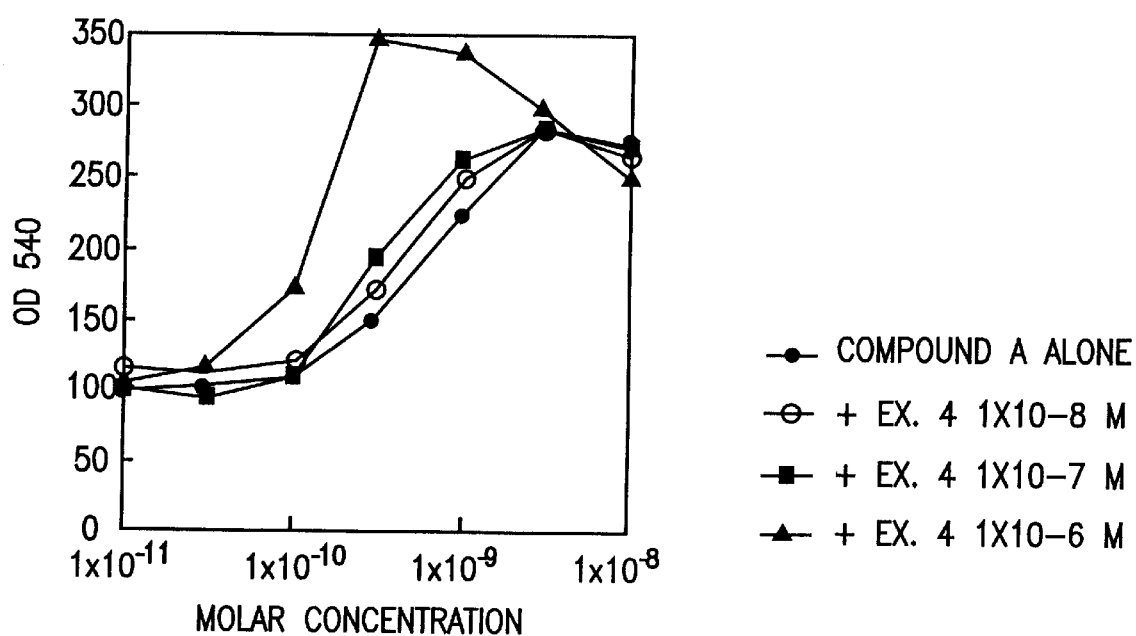

However, as can be seen from FIGS. 2 and 3, the Example 4 RXR-selective retinoid was able to potentiate the effects of all-trans retinoic acid and Compound A at concentrations where it was not active by itself. The potentiation was in the range of 3× to 10×, i.e., 3 to 10 times higher concentrations of all-trans retinoic acid or Compound A alone are required to obtain comparable levels of HL-60 differentiation.

From the results obtained it is obvious that the effects of RXR-selective ligands on HL-60 differentiation are more than additive and can therefore not be explained by residual RAR-activating effects. The observed effects are also somewhat more pronounced if a preferential RARα ligand (Compound A) rather than the less selective (RAR vs. RXR) all-trans RA is used. A potentiating effect is also compatible with in vitro data showing that RXR forms heterodimers with RAR which leads to an enhanced transcriptional activity on RAR-specific promoter sequences. It is not clear at the moment why relatively high concentrations of RXR-selective retinoids ($10^{-7}$M) are required to see any effects. These concentrations are above two orders of magnitude higher than the $EC_{50}$ in the RXR transcription activation assay, but it is not known whether the retinoid binding affinity of RXR changes upon heterodimer formation. Thus, ED50 values as shown in Table 1 might not be fully representative for effects mediated through heterodimers involving RXR.

EXAMPLE 19

The compound of Example 4 was tested for its ability to inhibit mouse B cell proliferation in combination with all-trans RA. The RXR selective ligand of the invention potentiated the inhibitory activity of all-trans RA on mouse B cell proliferation.

Materials and Methods
Retinoids

The binding and transactivation characteristics of the retinoids used in these studies are shown in the following table:

TABLE 2

| Retinoid | RARα binding $IC_{50}$ (nM) | RARα activation $ED_{50}$ (nM) | RXRα binding $IC_{50}$ (nM) | RXRα activation $ED_{50}$ (nM) |
|---|---|---|---|---|
| All-trans RA | 14 | 6.7 | >10,000 | 41 |
| Example 4 | >10,000 | >10,000 | 92 | 1.7 |

Cellular assays

Single cell suspensions of mouse spleen were set up in culture in flatbottomed 96 well Microtiter trays, 0.2 ml/well of a $2\times10^5$/ml cell suspension in IMDM supplemented with 10% foetal calf serum, HEPES, antibiotics and 50 μM 2-mercaptoethanol. The specific B cell mitogen *E. coli* lipopolysaccharide (DIFCO) (LPS) was added at 50μg/ml. Cultures were incubated at 37° C. in a humidified atmosphere and 5% $CO_2$.

The retinoids to be tested were first titrated in triplicate from 10 nM to 10 μM and left throughout the whole culture period. Subsequently, the active compounds were further titrated to reach the $IC_{50}$ values. Cyclosporin A (Sandoz AG) was used as a reference compound (from 1 nM to 1 μM).

After 2, 3 and 4 days of culture, the cells were pulsed with [$^3$H] thymidine, 1 μCi/well for 4 hours. The cultures were then harvested on glass fiber filters and the radioactivity imcorporated into DNA measured in a β-liquid scintillation counter (Betaplate, Wallac Oy, Turku, Finland).

The results are expressed as % of the response of untreated cultures. Mitogen-induced proliferation was measured as incorporation of $^3$H-thymidine after 24, 48 and 72 hours of culture. Retinoids were added to the cultures at the beginning of the culture period.

Results

1. Effect of RXR selective ligands on mouse B cell proliferation

Figure 4B:
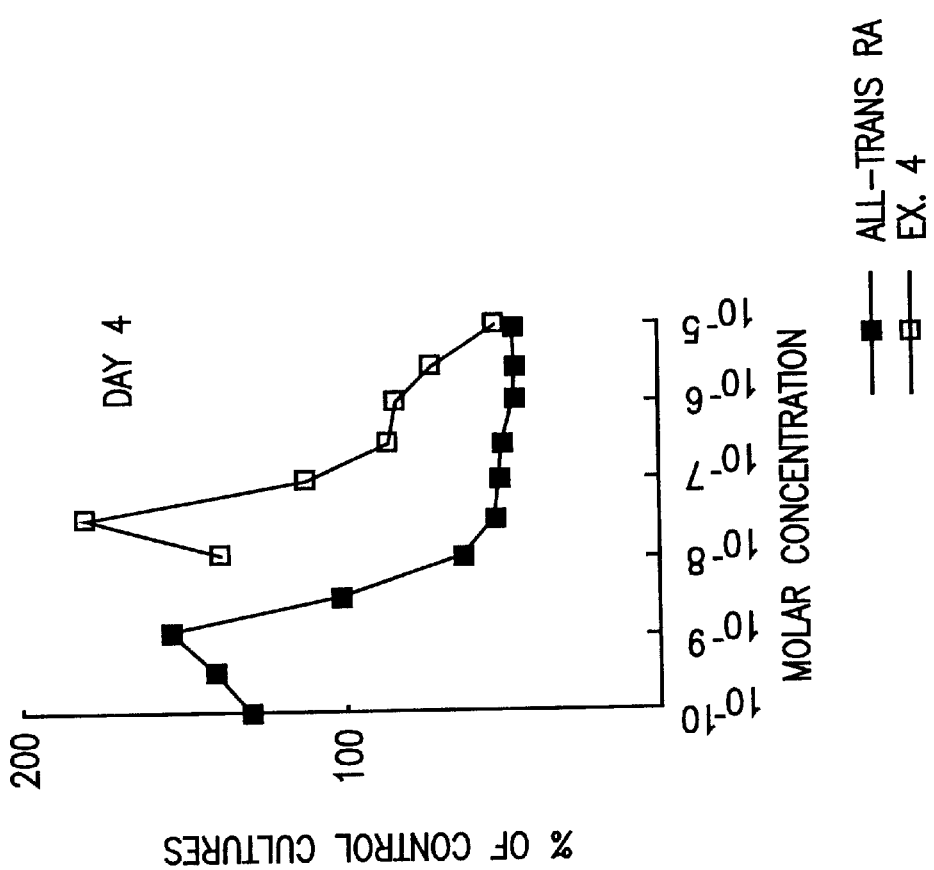
Figure 4A:
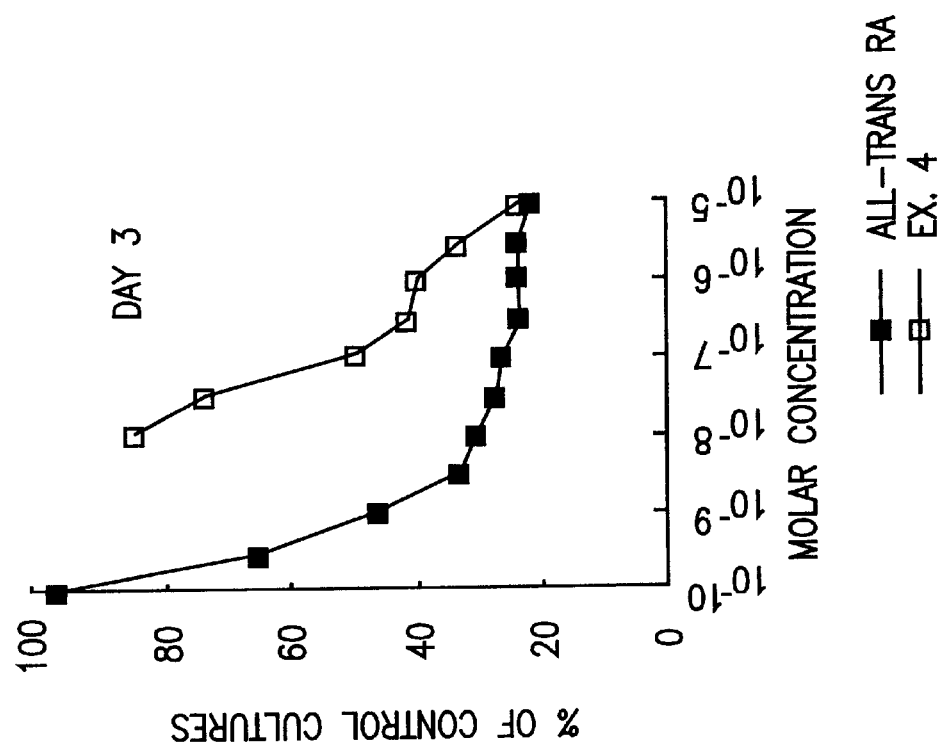

The RXR selective ligand of Example 4 was tested first for direct interference with LPS induced mouse B cell proliferation. The results are shown in FIG. 4 and demonstrate that the Example 4 retinoid is inhibitory, with an $IC_{50}$ of 100 nM. This potency is 1/100 of that of all-trans RA ($IC_{50}$=1 nM). At day 4, Example 4 at low doses (=$IC_{50}$ at day 3) is slightly enhancing the response, which is consistent with the results of all retinoids active in this system.

Figure 5:
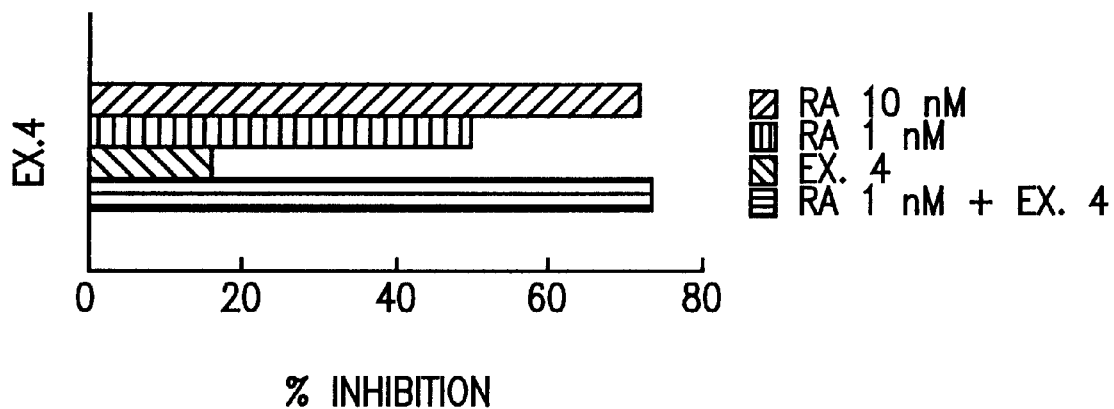

2. RXR selective ligands potentiate the inhibitory effect of all-trans retinoic acid on mouse B cell proliferation All-trans RA inhibits LPS induced mouse B cell proliferation with an $IC_{50}$ of 1 nM. Maximal inhibition is obtained with 10–30 nM and never exceeds 75–80%. The Example 4 RXR selective ligand of the invention was dosed into LPS stimulated cultures exposed to 1 nM of all-trans RA; cultures exposed to 10 nM of all-trans RA were set up in parallel. In all cases, concentrations of the Example 4 RXR ligand of the invention which are per se barely inhibitory induced a potentiation of the effect of 1 nM RA to the level observed with 10 nM RA. Similar results were obtained at day 2 and 3 of culture. The data of day 3 are as shown in FIG. 5. Because of the activity of the compound of Example 4, the effect is possibly an additive or enhancing. The results obtained at later points in culture, however, indicate that the effect is not simply additive, but rather an enhancement.

Figure 6:
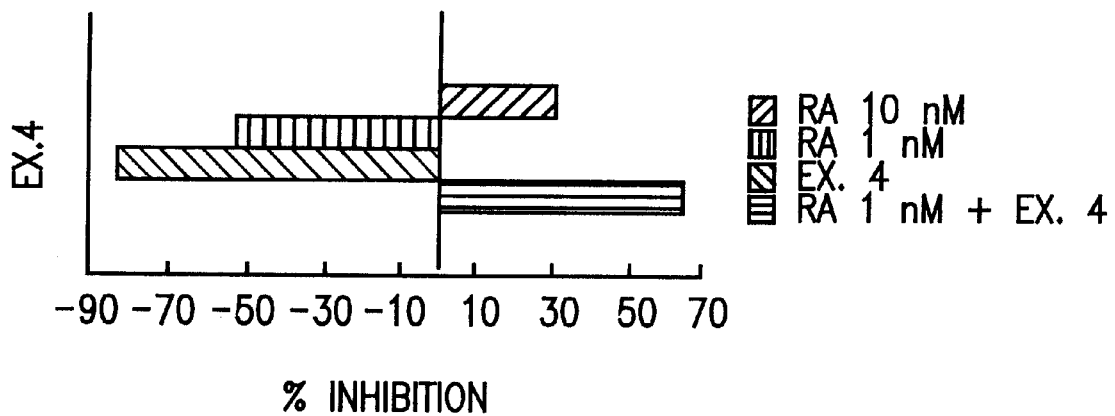

At day 4, 1 nM RA is not inhibitory any longer and actually induces a minor enhancement of the response, while 10 nM RA inhibits only about 30%. The reasons for this phenomenon are unknown, but the half life of the compound might play a role in it. The RXR selective ligand also has a similar effect (see curve of FIG. 4). However, the combination of 1 nM RA and the Example 4 RXR ligand of the invention still results in an inhibition on the order of that induced by 10 nM RA. The results are shown in FIG. 6.

The results demonstrate that an RXR selective retinoid (Example 4) potentiates the effect of all-trans RA in a functional system in which the retinoid effect is mediated by RARα. Potentiation is obtained with a 10 to 30 fold excess RXR ligand over all-trans RA. The magnitude of the potentiation is roughly tenfold: the level of inhibition usually induced by 10 nM RA is obtained with I nM RA in combination with the RXR ligand of the invention.

EXAMPLE 20

The following determinations using conventional assays of anti-acne activity demonstrate the anti-acne activity of compounds of the invention:

(1) Antiproliferative Activity on Human Sebocytes

Methods

Sebaceous cells were isolated from adult human sebaceous glands by a combination of enzymatic and mechanical methods (Doran et al., 1991). The cells were cultured in Iscove's medium containing 10% fetal calf serum and 4 μg/ml dexamethasone on a layer of growth-arrested 3T3 mouse fibroblasts. Cells were plated in medium without the test compound and then given test compound in fresh medium 24–48 hours after the initial plating. The cultures were given fresh medium, containing the test compound, every 48 hours. On the day of harvesting, the cultures were rinsed with 0.03% EDTA in PBS, to remove only the 3T3 fibroblasts. followed by incubation in 0.05% trypsin/0.03% EDTA. The cells were suspended, mixed vigorously to prepare a single cell suspension and counted in a hemocytometer.

Stock solutions of compounds were made up as 10–2 M solutions in 100% DMSO and stored at −20° C. in the dark. Compounds in solution were brought to room temperature and used by diluting directly into complete medium to the appropriate concentration.

The compounds were tested for the inhibition of proliferation of sebaceous cell growth in vitro at $10^{-6}$ and $10^{-7}$ M.

The compounds of Example 12, Example 2, and Example 4 were tested for their effects on inhibiting the proliferation of first passage human sebaceous cells in vitro after 10 days of exposure to drug. Results are reported as the concentration, in nM, required to inhibit growth by 50% ($IC_{50}$).

TABLE 3

| Inhibition of Human Sebaceous Cell Proliferation In Vitro | |
|---|---|
| Compound | $IC_{50}$ (nM) |
| Example 4 | >1000 (tested twice) |
| Example 2 | 100 and 1000 (tested twice) |
| Example 12 | 100 (tested twice) |
| 13-cis-retinoic acid | 100 |
| 9-cis-retinoic acid | 100 |

Example 4 displayed a poor dose response curve with suppression of growth reaching 30–40%. Although this is much weaker than 13-cis-retinoic acid, it is still indicative of biological activity in vitro. Example 2 gave an $IC_{50}$ of 100 nM for the first experiment although a 1000 nM dose only gave a 70 % inhibition of growth in that experiment.

(2) Rhino Mouse Utricle Reduction Activity

In this model compounds are examined for their ability to reduce the size of pre-existing utricles, keratinized pilosebaceous structures which resemble human comedones (Mezick et al., 1985).

Method

Female Rhino mice (hrrh hrrh), 6 to 8 weeks of age, obtained from Jackson Laboratories, were used in groups of 6. Compounds were dissolved in 100% acetone and stored at 4° C. for the duration of the experiment under nitrogen. The test compounds were applied to the dorsa of the mice daily for 5 days for 3 consecutive weeks. One day after the last dose, the mice were sacrificed by $CO_2$ inhalation. A flap of skin from the dorsum was cut out and incubated in 2M sodium bromide for 2–3 hours at room temperature. The epidermis was then separated from the dermis.

The epidermis was then dehydrated through 70%, 80%, 95%, 100% ethanol, and xylene. The samples were kept in each of the above solutions for 2 hours. The skin samples were removed from the xylene and mounted on glass microscope slides. Image analysis, using the Ultimage image analysis software, was used to determine the mean diameter and area of utricles. Approximately 5 fields per sample were examined, for an average of 150 utricles per mouse measured.

Results

Several compounds of the invention, Example 12, Example 2, and Example 4, were tested topically in the rhino mouse.

The mice were dosed topically with 100 μl of 13-cis retinoic acid, 9-cis retinoic acid, Example 12, Example 2, and Example 4 in acetone. The results are shown in Table 4, below:

TABLE 4

| Compound | Dose (μg/day) | Utricle Size (μm²/ utricle) | % Change from Control |
|---|---|---|---|
| Vehicle | | 9750 ± 508 | — |
| 13-cis-RA | 0.1 | 9187 ± 794 | $-6^{ns}$ |
| | 1 | 6400 ± 424 | −34 |
| | 10 | 3793 ± 368 | −61 |
| | 100 | 3132 ± 305 | −68 |
| 9-cis-RA | 0.1 | 8650 ± 427 | −11 |
| | 1 | 6926 ± 497 | −29 |
| | 10 | 3540 ± 354 | −64 |
| | 100 | 2644 ± 312 | −73 |
| Example 12 | 0.1 | 9104 ± 829 | $-7^{ns}$ |
| | 1 | 9156 ± 938 | $-6^{ns}$ |
| | 10 | 7634 ± 485 | −22 |
| | 100 | 3596 ± 300 | −63 |
| Example 2 | 0.1 | 9535 ± 890 | $-2^{ns}$ |
| | 1 | 9616 ± 1134 | $-1^{ns}$ |
| | 10 | 9049 ± 891 | $-7^{ns}$ |
| | 100 | 5437 ± 615 | −44 |
| Example 4 | 0.1 | 9843 ± 565 | $+1^{ns}$ |
| | 1 | 9491 ± 507 | $-3^{ns}$ |
| | 10 | 8951 ± 964 | $-8^{ns}$ |
| | 100 | 5916 ± 992 | −39 |

$^{ns}$=not statistically significant from controls, all other p values <0.05.

NOTES:

During this experiment several side effects were noticed. The 100 μg 13-cis-retinoic acid-dosed animals displayed exfoliation and erythema on day 5. The 9-cis-retinoic acid-dosed animals showed these effects a day earlier at the same dose.

On day 7 of dosing, erythema was seen for 100 μg Example 12. There was some erythema noticed on the 100 μg Example 2 animals on the same day. However, the erythema was not as intense as that for Example 12. At this same time point, the comparable dose of Example 4 showed no appreciable erythema.

By the 14th day of dosing there was exfoliation seen on all 100 μg Example 12-dosed animals which was not seen the day before. If the compounds are rank-ordered for the 100 μg concentration with respect to exfoliation/erythema from most severe to least severe, the order would be: 9-cis-RA, 13-cis-RA, Example 12, Example 2, and Example 4.

Thus, the compounds of the invention produced reduced irritation in comparison to 9-cis-RA, 13-cis-RA.

(3) In vivo Effect of Compounds on the Size of Sebaceous Glands of Golden Syrian Hamsters Methods Charles River Golden Syrian male hamsters were given the desired dose in acetone. The compounds were stored at 4° C. protected from light. Fresh solutions were made up weekly.

Hamsters were dosed daily for five days, rested for two days, and dosed again for five days until 20 doses were given. The volume of solution was 50 microliters per ear.

Hamsters were sacrificed by $CO_2$ inhalation, and the ears removed for histological evaluation. One ear was removed and the ventral surface separated from the rest of the ear. A 2 mm punch was removed 5 mm from the tip of the ear and stained in 0.1 % Sudan Black B dissolved in 100% propylene glycol overnight. After destaining, the size of sebaceous glands was quantified with a Donsanto Image Analysis System.

Data are given as the average area of 80–120 sebaceous glands per dose, as percent of the control (solvent-treated) sections.

TABLE 5

Effect of 4 Weeks Topical Dosing with the compound of Example 4 and 13-cis-retinoic acid on Hamster Ear Sebaceous Gland Size

| Compound | Dose (μg/day) | Sebaceous Gland Size | % Change from Control |
|---|---|---|---|
| Vehicle | — | 16475 ± 1708 | — |
| 13-cis-RA | 1 | 14029 ± 2977 | $-15^{ns}$ |
| | 10 | 12965 ± 2029 | −21 |
| | 100 | 10459 ± 1302 | −37 |
| Example 4 | 1 | 13237 ± 1491 | −20 |
| | 10 | 17046 ± 4667 | $+3^{ns}$ |
| | 100 | 13043 ± 1577 | −21 |

$^{ns}$=not statistically significant from controls. All other values significant from vehicle controls.

References

Doran et al., "Characterization of human sebaceous cells in vitro., J. Invest. Dermatol. 96:341–348 (1991).

Mezick et al., "Topical and systemic effects of retinoids on horn-filled utriculus size in the rhino mouse. A model to quantify 'antikeratinizing' effects of retinoids.", J. Invest. Dermatol, 83:110–113 (1985).

EXAMPLE 21

The compound of Example 6 was tested for its ability to inhibit a human breast carcinoma cell line in combination with a retinoid having RARα activity, all-E-3,7-dimethyl-9-[(2-methoxy-4-methyl-6-octyloxy)phenyl]-2,4,6,8-nonatetraenoic acid (Compound B), as shown:

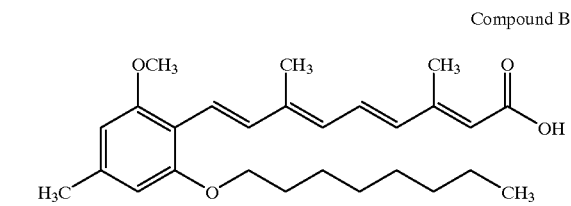

Compound B

The results demonstrated that the RXR selective ligand of the invention potentiated the solid tumor inhibitory activity of Compound B.

1. Synthesis of Compound B

Compound B was prepared in accordance witht the following procedure:

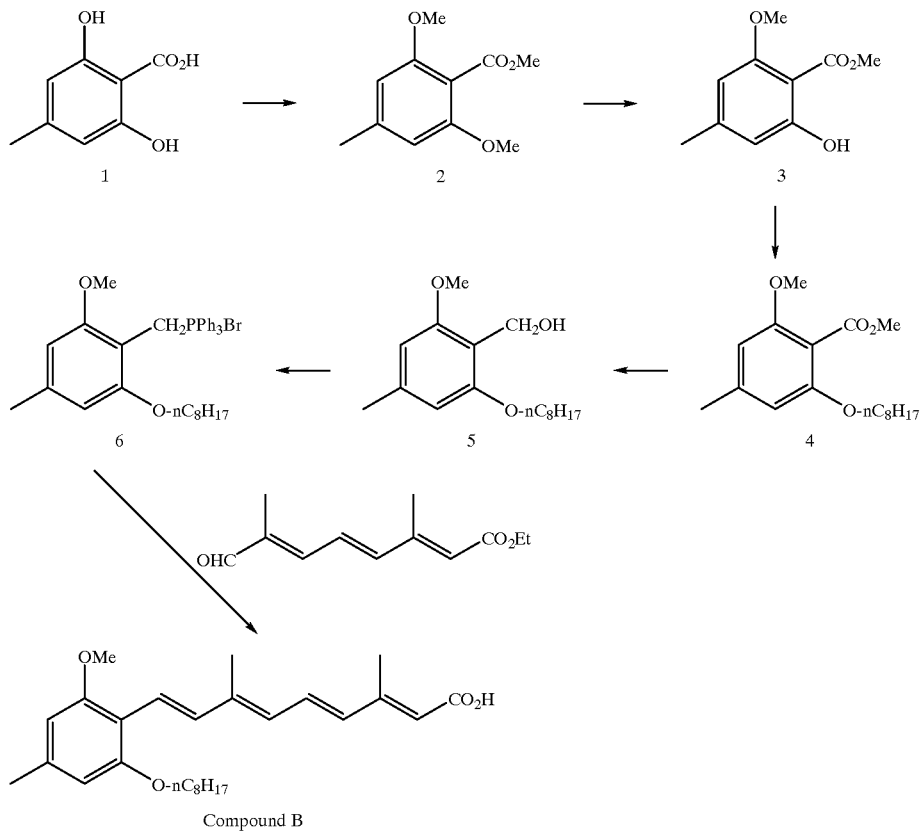

Compound B

A solution of 2,6-dihydroxy-4-methyl-benzoic acid 1 in acetone (50.4 g; 750 ml) was treated with methyl iodide (100 ml) and potassium carbonate (124.2 g) and heated at reflux for 18 hours. The mixture was then cooled to room temperature and filtered free of solids. Concentration of the solution gave the crude product which was dissolved in ethylacetate and washed with aqueous sodium hydroxide solution (IN; cold). Removal of the solvents in vacuo then gave methyl 2,6-dimethoxy-4-methyl -benzoate 2 (54 g). This material (52.5 g) was disolved in dichloromethane (1000 ml) cooled to −70° C. and treated with a solution of borontrichloride in the same solvent (29.3 g/100 ml; 180 ml). This mixture was then warmed up to room temperature and stirred for a further 45 minutes and then poured onto ice. The organic layer was separated, washed with more water, dried (magnesium sulphate), filtered and concentrated. The residue was then purified by high performance preparative liquid chromatography (HPLC) using a Waters prep.500 chromatograph (7% ethyl acetate/hexane eluent) to give pure methyl 2-hydroxy-6-methoxy-4-methyl benzoate 3 as a solid (28.3 g). A solution of this material (35 g) in methyl ethyl ketone (700 ml) containing potassium carbonate (27.1 g) was treated with 1-octyliodide (34.2 g) and heated at reflux for 20 hours. The reaction mixture was cooled, filtered free of solids and the filterate was concentrated and then redisolved in a mixture of hexane and ethyl acetate. This solution was then washed with aqueous base (IN sodium hydroxide), water, dried (magnesium sulphate) and concentrated to dryness. Puification by HPLC as before gave pure methyl 2-methoxy-6-octyloxy-4-methyl-benzoate 4 (51.8 g). A solution of this material (51.8 g) in toluene (500 ml) was cooled to −60° C. and treated with a solution of diisobutyalumninium hydride ( 25% in hexane; 281 ml) and then warmed to room temperature. The reaction mixture was then carefully treated with aqueous methanol (100 ml; 1:1) with cooling so that the temperature was kept at 20° C. followed by the addition of hexane (500 ml) and magnesium sulphate. The solids were then filtered off and the solvents were removed in vacuo to yield the crude alcohol 5. This material (47 g) was dissolved in acetonitrile (500 ml) containing triphenylphosphoniumhydrobromide (54.9 g) and heated at reflux for 22 hours. The solvents were then removed in vacuo and the crude salt 6 was dried at room temperature at 0.1 mm Hg pressure (this material can be crystallised from tetrahydrofuran to give pure [(2-methoxy-6-octyloxy-4-methyl)phenyl]methyl-triphenylphosphonium bromide). This salt 6 was then converted into Compound B, all-E-3,7-dimethyl-9-[(2-methoxy-4-mthyl-6-octyloxy) phenyl]-2,4,6,8-nonatetraenoic acid, as described in U.S. Pat. No. 4,894,480 (example 5).

2. Testing

Retinoid receptor binding and transactivation assays were performed on Compound B and Example 6 as described above. The results were as follows:

TABLE 6

| Compound | | Activation | | | | Binding | | |
|---|---|---|---|---|---|---|---|---|
| | | RAR | | RXR | | RAR | | RXR |
| | | EC$_{50}$ (nM) | % max | EC$_{50}$ (nM) | % max | IC$_{50}$ (nM) | % | IC$_{50}$ (nM) |
| B | α | 11 | 114 | @ 1000 | 0 | 240 | — | |
| | β | 5.3 | 82 | | | 500 | — | |
| | γ | @ 1000 | 48 | | | >10,000 | <20 | |
| Ex. 6 | α | @ 1000 | 4 | 1.4 | — | >10,000 | 24 | 110 |
| | β | @ 1000 | 8 | | | >10,000 | 9 | — |
| | γ | @ 1000 | 9 | | | >10,000 | 245 | 150 |

Breast carcinoma cell line, T47-D, obtained from the ATCC [Accession No. HTB133] was grown in RPMI 1640 media supplemented with 10% FBS, 10 μg/ml insulin and 13 ng/ml gentamicin, and incubated at 37° C., 4.5% $CO_2$ and 95.5% humidified air. The cells were harvested upon reaching 70–80% confluency and pelleted. The cells were resuspended in the media and seeded (150 μl/well) into 96-well plates (Corning) at a density allowing linear growth over a seven day assay period (i.e., T47-D seeded at $4 \times 10^3$ cells/well). Plates were placed in an incubator at 37° C. overnight.

Drugs (1 mM stock in 100% DMSO) were added 18–24 hours post-seeding. Drug combinations were prepared in 96-well microtiter plates and manually added to the assay plates. MTT assays were performed at days 3–7 post drug addition. The MTT assay is a tetrazolium-based assay which measures the viability of cells in culture. MTT (3-[4,5-dimethylthiazol-2-yl-2,5-diphenyltetrazolium bromide) stock solution (5 mg/ml in 1× PBS) was added to assay plates (50 μl/well) and incubated for 2.5 hours at 37° C.

Liquid was removed by aspiration, 50 μl 95% ethanol was added, and the plates were shaken (Mini-Orbital Shaker, Bellco) for 15 minutes to solubilize the formazan product. The optical density of each well was measured using an automatic plate reader (Microplate EL320 Reader, Bio-Tek Instruments) with a test wavelength of 570 nm and a reference wavelength of 660 nm. The amount of cell growth inhibition caused by various concentrations of Compound B in combination with a constant concentration of the compound of Example 6 was determined in accordance with the following equation:

$$\% \text{ Inhibition} = \frac{OD_{570}(\text{untreated}) - OD_{570}(\text{drug treated})}{OD_{570}(\text{untreated})} \times 100$$

Figure 7:
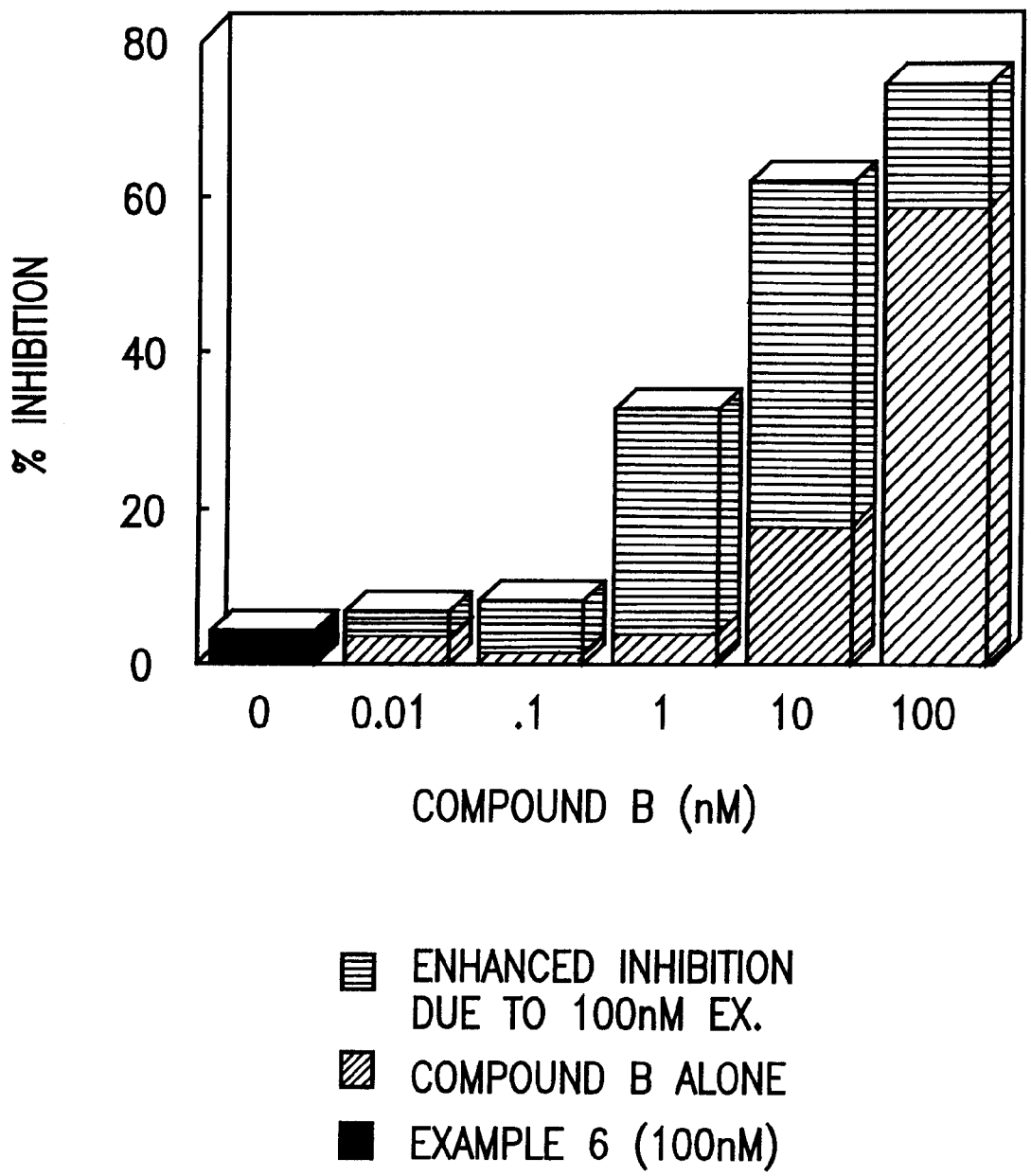

The results are shown graphically in FIG. 7. The results demonstrate that the RXR-selective compound of the invention potentiates the activity of a retinoid having RARα activity in inhibiting the growth of a solid tumor cell line.

EXAMPLE A

Hard Gelatine capsules containing 20 mg. active substance:

Composition: One Capsule contains:

| | |
|---|---|
| Formula I | 20 mg. |
| RARα retinoid | 20 mg |
| Gelatine Bloom 30 | 70.0 mg. |
| Maltodextrin MD 05 | 108.0 mg. |
| dl-α-Tocopherol | 2.0 mg. |
| Sodium ascorbate | 10.0 mg. |
| Microcrystalline cellulose | 48.0 mg. |
| Magnesium stearate | 2.0 mg. |
| (weight capsule content) | 280.0 mg. |

Procedure:

The active substances are wet milled in a solution of gelatine, maltodextrin, dl-α-Tocopherol and sodium ascorbate.

The wet milled suspension is spray-dried

The spray-dried powder is mixed with microcrystalline cellulose and magnesium stearate.

280 mg. each of this mixture are filled into hard gelatine capsules of ble size and color.

We claim:

1. A compound having the formula:

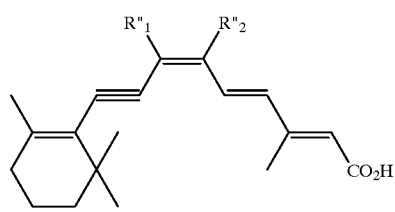

III wherein $R''_1$ and $R''_2$ are independently lower alkyl, or a pharmaceutically acceptable salt, ester or amide thereof.

2. A compound having the formula:

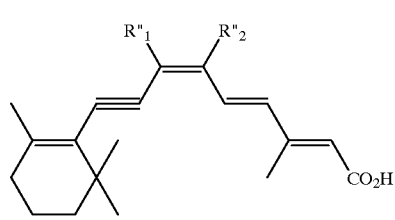

III wherein $R''_1$ and $R''_2$ taken together are $C_{3-13}$-alkylene in which one carbon atom may be substituted by a heteroatom selected from the group consisting of sulfur, oxygen and nitrogen, or a pharmaceutically acceptable salt, ester or amide thereof.

3. A compound having the formula:

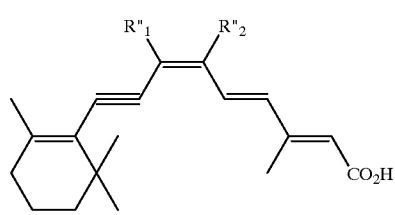

III wherein $R''_1$ and $R''_2$ taken together with the carbon atoms to which they are attached are an aromatic ring having from 5–6 carbon atoms or a heteroaromatic ring having from 5–6 atoms in which one atom of $R''_1$ or $R''_2$ is a heteroatom selected from the group consisting of oxygen, nitrogen and sulfur and the remaining atoms of $R''_1$ and $R''_2$ are carbon, or a pharmaceutically acceptable salt, ester or amide thereof.

4. (2E,4E)-3-methyl-5-(2-((E)-2(2,6,6-trimethyl-1-cyclohexen-1-yl)ethenyl)-1-cyclohepten-1-yl)-2,4-pentadienoic acid.

5. (2E,4E)-3-Methyl-5-(2-((E)-2(2,6,6-trimethyl-1-cyclohexen-1-yl)ethenyl)-1-cycloocten-1-yl)-2,4-pentadienoic acid.

6. The compound of claim 2 wherein $R''_1$ and $R''_2$ taken together are $C_{3-13}$-alkylene.

7. The compound of claim 6 wherein $R''_1$ and $R''_2$ taken together are $C_{3-6}$-alkylene.

8. The compound of claim 7 wherein said compound is (2E,4E)-3-Methyl-5-[2-(2,6,6-trimethyl-cyclohex-1-enylethynyl)-cyclopent-1-enyl]-penta-2,4-dienoic acid.

9. The compound of claim 7 wherein said compound is (2E,4E)-3-Methyl-5-[2-(2,6,6-trimethyl-cyclohex-1-enylethynyl)-cyclohept-1-enyl]-penta-2,4-dienoic acid.

10. The compound of claim 3 wherein said ring is selected from the group consisting of thiophene, benzene and pyridine.

11. The compound of claim 10 wherein said compound is (2E,4E)-3-Methyl-5-[2-(2,6,6-trimethyl-cyclohex-1-enylethynyl)-phenyl]-penta-2,4-dienoic acid.

* * * * *